United States Patent [19]

Janssens et al.

[11] Patent Number: 4,634,704
[45] Date of Patent: Jan. 6, 1987

[54] ANTI-ALLERGIC FIVE MEMBERED HETEROCYCLIC RING CONTAINING N-(BICYCLIC HETEROCYCYL)-4-PIPERIDINAMINES

[75] Inventors: Frans E. Janssens, Bonheiden; Joseph L. G. Torremans, Beerse; Jozef F. Hens, Nijlen; Theophilus T. J. M. Van Offenwert, Vosselaar, all of Belgium

[73] Assignee: Janssen Pharmaceutica, N.V., Beerse, Belgium

[21] Appl. No.: 625,343

[22] Filed: Jun. 27, 1984

Related U.S. Application Data

[63] Continuation-in-part of Ser. No. 539,597, Oct. 6, 1983, abandoned.

[51] Int. Cl.$^4$ .................. A61K 31/445; C07D 401/00
[52] U.S. Cl. .................................. 514/253; 514/212; 514/269; 514/303; 514/316; 514/321; 514/322; 514/323; 514/326; 514/333; 514/357; 514/405; 546/118; 546/187; 546/194; 546/199; 540/597; 540/598
[58] Field of Search .............. 546/118, 187, 194, 199; 544/333, 357, 405; 514/253, 269, 303, 316, 212, 322, 321, 323, 326; 260/243.3, 244.4, 245.5, 245.6

[56] References Cited

U.S. PATENT DOCUMENTS 4,219,559 8/1980 Janssens et al. ............... 546/118

Primary Examiner—Henry R. Jiles
Assistant Examiner—Bernard I. Dentz
Attorney, Agent, or Firm—Geoffrey G. Dellenbaugh

[57] ABSTRACT

Five membered heterocyclic ring containing N-(bicyclic heterocyclyl)-4-piperidinamines having histamine and serotonine antagonistic activity which compounds are useful agents in the treatment of allergic diseases.

6 Claims, No Drawings

ANTI-ALLERGIC FIVE MEMBERED HETEROCYCLIC RING CONTAINING N-(BICYCLIC HETEROCYCYL)-4-PIPERIDINAMINES

CROSS-REFERENCE TO RELATED APPLICATIONS

This is a continuation-in-part of our co-pending application Ser. No. 539,597 filed Oct. 6, 1983, now abandoned.

BACKGROUND OF THE INVENTION

In U.S. Pat. No. 4,219,559 there are described a number of N-heterocyclyl-4-piperidinamines having the formula

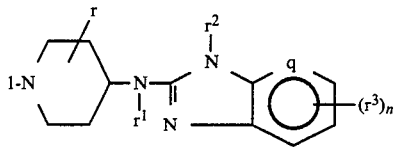

which compounds are useful as antihistaminic agents.

The compounds of the present invention differ from the prior art compounds essentially by the nature of the 1-piperidinyl substituent and by the fact that the compounds of the present invention are not only potent histamine-antagonists but also potent serotonin-antagonists.

DESCRIPTION OF THE PREFERRED EMBODIMENTS

This invention is concerned with novel N-heterocyclyl-4-piperidinamines which may structurally be represented by the formula

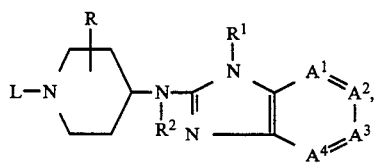

the pharmaceutically acceptable acid addition salts and the possible stereochemically isomeric forms thereof, wherein:

$A^1=A^2—A^3=A^4$ is a bivalent radical having the formula

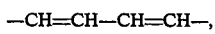 (a)

 (b)

 (c)

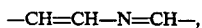 (d)

or

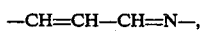 (e)

wherein one or two hydrogen atoms in said radicals (a)-(e) may, each independently from each other, be replaced by halo, lower alkyl, lower alkyloxy, trifluoromethyl or hydroxy;

R is a member selected from the group consisting of hydrogen and lower alkyl;

$R^1$ is a member selected from the group consisting of hydrogen, alkyl, cycloalkyl, $Ar^1$ and lower alkyl substituted with one or two $Ar^1$ radicals;

$R^2$ is a member selected from the group consisting of hydrogen, lower alkyl, cycloalkyl, (lower alkyl)—CO—, (lower alkyloxy)—CO— and $Ar^2$—lower alkyl;

L is a member selected from the group consisting of a radical of formula

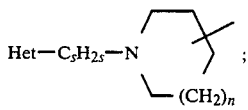 (f)

a radical of formula

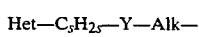 (g);

and a radical of formula

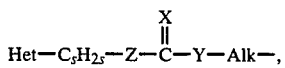 (h)

wherein n is 0 or the integer 1 or 2;
s is 0 or an integer of from 1 to 6 inclusive;
Alk is lower alkanediyl;
Y is O, S, $NR^3$ or a direct bond;
X is O, S, $CH—NO_2$ or $NR^4$;
Z is O, S, $NR^5$ or a direct bond; and
Het is an optionally substituted 5-membered heterocyclic ring having at least one nitrogen atom and being optionally condensed with an optionally substituted benzene ring, said Het being connected to $C_sH_{2s}$ on a carbon atom;
said $R^3$ being hydrogen, lower alkyl, $(Ar^2)$lower alkyl, 2-lower alkyloxy-1,2-dioxoethyl or a radical of formula —C(=X)—$R^6$, $R^6$ being hydrogen, lower alkyl, $Ar^2$, $Ar^2$—lower alkyl, lower alkyloxy, $Ar^2$—lower alkyloxy, mono- or di(lower alkyl)amino, $Ar^2$—amino, $Ar^2$—lower alkylamino or $Ar^2$—lower alkyl(lower alkyl)amino;
said $R^4$ being hydrogen, lower alkyl, cyano, nitro, $Ar^2$—sulfonyl, lower alkylsulfonyl, lower alkylcarbonyl or $Ar^2$—carbonyl; and
said $R^5$ being hydrogen or lower alkyl; provided that:
(i) when $A^1=A^2—A^3=A^4$ is a bivalent radical of formula (a) or (b), then Het is other than 1-(lower alkyl)pyrrolyl;
(ii) when $A^1=A^2—A^3=A^4$ is a bivalent radical of formula (a) or (b) and L is a radical of formula (g) wherein s is 0 and Y is $NR^3$, then Het is other than 1H-benzimidazol-2-yl;
wherein $Ar^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and lower alkyl—CO—; thienyl; halothienyl; furanyl; lower alkyl substituted furanyl; pyridinyl; pyrazinyl; thiazolyl and imidazolyl optionally substituted by lower alkyl; and wherein $Ar^2$ is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)—CO.

As used in the foregoing definitions the term halo is generic to fluoro, chloro, bromo and iodo; the term "lower alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "alkyl" is meant to include lower alkyl radicals, as defined hereinabove, and the higher homologs thereof having from 7 to 10 carbon atoms; the term "cycloalkyl" is generic to cyclopropyl, cyclobutyl, cyclopentyl and cyclohexyl; and "lower alkanediyl" is meant to include bivalent straight or branch chained alkanediyl radicals having from 1 to 6 carbon atoms.

It is evident that in the compounds of formula (I), the Het-ring may be unsaturated or partly or completely saturated.

The compounds of formula (I) wherein Het is a heterocycle which is substituted with a hydroxy, mercapto or amino radical may contain in their structure a keto-enol tautomeric system or a vinylog system thereof and consequently these compounds may be present in their keto form as well as their enol form.

Preferred compounds within the invention are those wherein Het is a member selected from the group consisting of thiazolyl, 4,5-dihydrothiazolyl, oxazolyl, imidazolyl, tetrazolyl, 1,3,4-thiadiazolyl, benzimidazolyl, benzothiazolyl, benzoxazolyl, and indolyl whereby each of the said Het-radicals may optionally be substituted where possible with up to two substituents selected from the group consisting of lower alkyl, $Ar^1$, $Ar^1$—lower alkyl, amino, (aminoiminomethyl)amino, mono- and di(lower alkyl)amino, $Ar^1$—amino, nitro and pyrimidinyl.

Particularly preferred compounds are those wherein L is a radical (g) or (h) wherein Het is as described hereinabove for the preferred compounds.

In order to simplify the structural representations of the compounds of formula (I) and of certain precursors and intermediates thereof, the

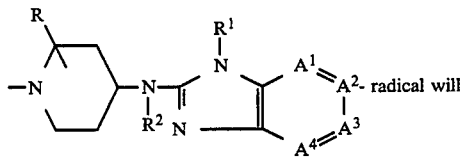 radical will hereafter be represented by the symbol D.

The compounds of formula (I) can generally be prepared by reacting an intermediate of formula (II) with a piperidine of formula (III) following art-known alkylating procedures.

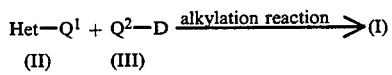

In (II) and (III) Het is as previously described and $Q^1$ and $Q^2$ are selected so that in combination with Het a bivalent radical of formula (f), (g) or (h) is formed during the alkylation reaction, said (f), (g) and (h) having the previously described meaning. For example, the compounds of formula (I) can generally be prepared by N-alkylating a piperidine of formula (III) wherein $Q^2$ is hydrogen, said piperidine being represented by the formula (III-a), with a reagent of formula (II) having the general formula L-W, (II-a).

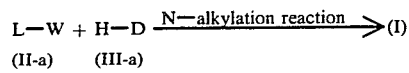

In (II-a) W represents an appropriate reactive leaving group such as, for example, halo, e.g., chloro, bromo or iodo, or a sulfonyloxy group, e.g. methylsulfonyloxy or 4-methylphenylsulfonyloxy.

Additionally, the compounds of formula (I) wherein L is a radical of formula (f), a radical of formula (g) wherein Y is other than a direct bond, Y', or a radical of formula (h) wherein Z is other than a direct bond, Z', said compounds being represented by the formulae (I-a-1), respectively (I-a-2) and (I-a-3), can be prepared by alkylating a piperidine of formula (III-b) with a reagent of formula (II-b).

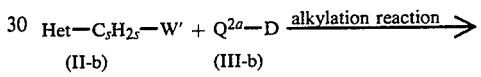

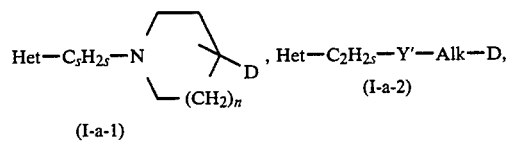

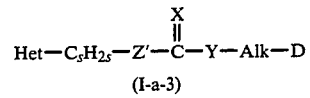

In (III-b) $Q^{2a}$ is a radical of formula

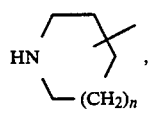

respectively a radical of formula HY'—Alk— or

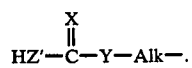

In (II-b) W' has the previously defined meaning of W and, where s is 0, it may also represent a lower alkyloxy or lower alkylthio group.

The compounds of formula (I-a-2) may also be prepared by alkylating a piperidine of formula (III) wherein $Q^2$ is a radical of formula —Alk—W, said piperidine being represented by the formula (III-c), with a reagent of formula (II) wherein $Q^1$ is a radical of formula —$C_sH_{2s}$—Y'H, said reagent being represented by the formula (II-c).

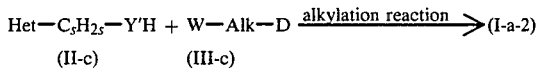

The compounds of formula (I) wherein L is a radical of formula Het—C$_s$H$_{2s}$—Z—C(=X)—Y'—Alk, said compounds being represented by the formula (I-a-4), may also be prepared by N-alkylating a piperidine of formula (III-c) with a reagent of formula (II) wherein Q$^2$ is a radical of formula —C$_s$H$_{2s}$—Z—C(=X)—Y'H, said reagent being represented by the formula (II-d).

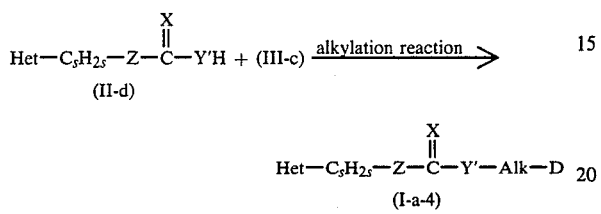

The alkylation reactions are conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; N,N-dimethylformamide (DMF); N,N-dimethylacetamide (DMA); nitrobenzene; 1-methyl-2-pyrrolidinone; dimethyl sulfoxide (DMSO); and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. Somewhat elevated temperatures may enhance the rate of the reaction.

The compounds of formula (I) can also be prepared by the cyclodesulfurization reaction of an appropriate thiourea derivative of the formula

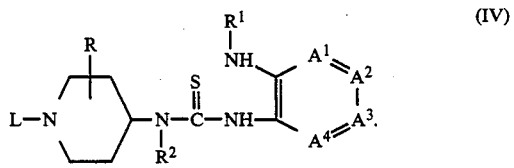

Said cyclodesulfurization reaction may be carried out by the reaction of (IV) with an appropriate alkyl halide, preferably iodomethane in an appropriate reaction-inert organic solvent, e.g., a lower alkanol such as methanol, ethanol, 2-propanol and the like. Otherwise, the cyclodesulfurization reaction may be carried out by the reaction of (IV) with an appropriate metal oxide or salt in an appropriate solvent according to art-known procedures. For example, the compounds of formula (I) can easily be prepared by the reaction of (IV) with an appropriate Hg(II) or Pb(II) oxide or salt, such as, for example H$_g$O, HgCl$_2$, Hg(OAc)$_2$, PbO or Pb(OAc)$_2$. In certain instances it may be appropriate to supplement the reaction mixture with a small amount of sulfur. Even so methanediimines, especially N,N'-methanetetraylbis[cyclohexanamine] may be used as cyclodesulfurizing agents.

The compounds of formula (I) wherein L is a radical of formula (h) wherein Z is Z', Y is NH and X is O or S, said X being represented by X' and said compounds by the formula (I-b-1), can generally be prepared by reacting an isocyanate or isothiocyanate of formula (VI) with a reagent of formula (V).

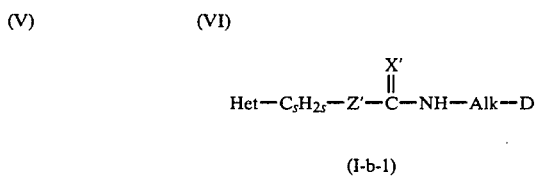

The compounds of formula (I) wherein L is a radical of formula (h) wherein Z is NH, Y is Y' and X is X', said compounds being represented by the formula (I-b-2), can be prepared by reacting an isocyanate or isothiocyanate of formula (VII) with a piperidine of formula (VIII).

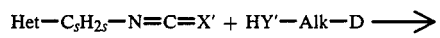

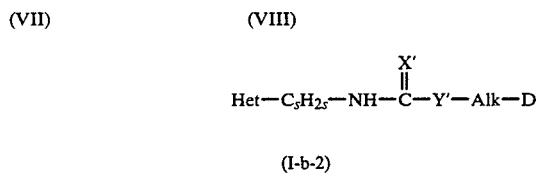

The reaction of (V) with (VI) and (VII) with (VIII) is generally conducted in a suitable reaction-inert solvent such as, for example, an ether, e.g., tetrahydrofuran and the like. Elevated temperatures may be suitable to enhance the rate of the reaction.

The compounds of formula (I) wherein L is a radical of formula (h) wherein Z is a direct bond and X is X', said compounds being represented by the formula (I-c), may be prepared by reacting a piperidine of formula (VIII) with a reagent of formula (IX).

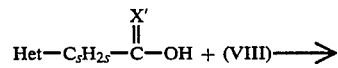

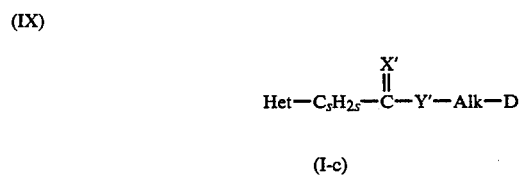

The reaction of (VIII) with (IX) may generally be conducted following art-known esterification- or amidation reaction procedures. For example, the carboxylic acid may be converted into a reactive derivative, e.g., an anhydride or a carboxylic acid halide, which subsequently, is reacted with (VIII); or by reacting (VIII) and (IX) with a suitable reagent capable of forming amides or esters, e.g., dicyclohexylcarbodiimide, 2-chloro-1-methylpyridinium iodide and the like. Said reactions are most conveniently conducted in a suitable solvent such as, for example, an ether, e.g. tetrahydrofuran, a halogenated hydrocarbon, e.g. dichloromethane, trichloromethane or a polar aprotic solvent, e.g. N,N-dimethylformamide. The addition of a base, e.g. N,N-diethylethanamine may be appropriate.

The compounds of formula (I) wherein L is a radical of formula (g) wherein Y is a direct bond and s is 0, said compounds being represented by the formula (I-d), may also be prepared by reacting an alkenylene of formula (X) with a piperidine of formula (III-a) by stirring and, if desired, heating the reactants together, optionally in the presence of a suitable solvent.

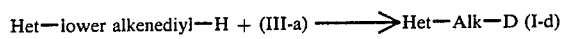

Het—lower alkenediyl—H + (III-a) ———>Het—Alk—D (I-d)

The compounds of formula (I) may also be prepared following procedures for preparing five-membered ring heterocycles which are known in the art, or analogous procedures thereof. A number of such cyclization procedures will be described hereinafter.

The bivalent radical K used in the description of these cyclization reactions has the following meaning.

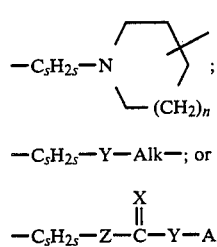

$-C_sH_{2s}-N\begin{matrix}\\\\(CH_2)_n\end{matrix}$ ; (i)

$-C_sH_{2s}-Y-Alk-$; or (j)

$-C_sH_{2s}-Z-\overset{X}{\underset{\|}{C}}-Y-Alk-$, (k)

For example, the compounds of formula (I), wherein Het is an optionally substituted imidazolyl radical, said compounds being represented by the formula (I-e), may be prepared by the cyclization reaction of an appropriate N-(2,2-dilower alkyloxyethyl)imidamide derivative of the formula (XI).

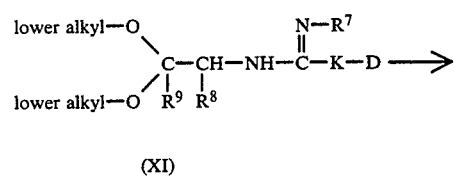

(XI)

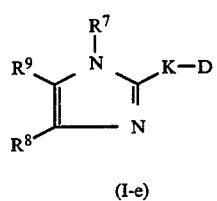

(I-e)

wherein and $R^7$, $R^8$ and $R^9$ are each independently optional substituents of the imidazole ring.

The cyclization reaction may conveniently be conducted in a suitable solvent in the presence of an appropriate acid such as, for example hydrochloric-, hydrobromic-, sulfuric- or phosphoric acid. Elevated temperatures may enhance the rate of the reaction.

Further, the compounds of formula (I) wherein Het is an optionally substituted 1H-benzimidazol-2-yl radical, said compounds being represented by the formula (I-f), may be prepared by the cyclodesulfurization reaction of an appropriate derivative of the formula (XII).

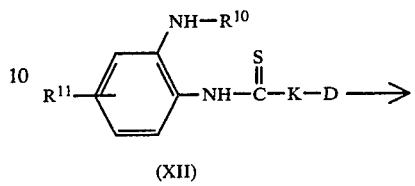

(XII)

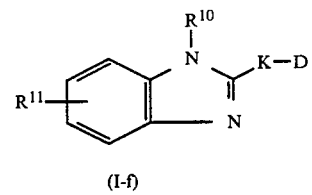

(I-f)

wherein $R^{10}$ and $R^{11}$ are each independently optional substituents of the 1H-benzimidazol-2-yl ring.

Said cyclodesulfurization reaction may be carried out following the same procedures as described hereinabove for the preparation of (I) starting from (IV).

The compounds of formula (I), wherein Het is an optionally substituted oxazolyl radical, said compounds being represented by the formula (I-g), may be prepared by reacting a reagent of formula (XIII) with an intermediate of formula (XIV).

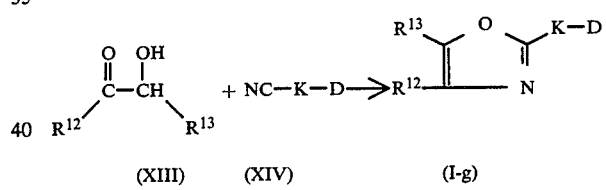

(XIII)   (XIV)   (I-g)

wherein $R^{12}$ and $R^{13}$ are each independently optional substituents of the oxazole ring.

The reaction of (XIII) and (XIV) may conveniently be conducted in a suitable solvent or mixture of solvents in the presence of an appropriate base such as, for example, an alkali metal- or earth alkaline metal hydroxide, carbonate, hydrogen carbonate and the like, e.g. sodium hydroxide, sodium carbonate, potassium hydrogen carbonate and the like. Suitable solvents or solvent mixtures are, for example, water, tetrahydrofuran, N,N-dimethylformamide, N,N-dimethylacetamide, 2-propanone, and the like, and mixtures thereof.

The compounds of formula (I), wherein Het is an optionally substituted thiazolyl radical, may be prepared by a number of condensation reactions, yielding, depending on the case, compounds which may be represented by the formulae (I-h), (I-i) and (I-j).

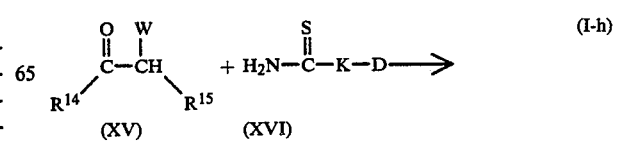

(XV)   (XVI)

(I-h)

$$\begin{array}{c} R^{15} \diagdown \hspace{-3pt} \diagup S \diagdown \hspace{-3pt} \diagup K-D \\ \| \\ R^{14} \diagdown \hspace{-3pt} \diagdown N \end{array}$$

$$\underset{(XVII)}{\overset{S}{\underset{\|}{R^{16}-C-NH_2}}} + \underset{(XVIII)}{\overset{R^{17}}{\underset{|}{W-CH-C-K-D}}} \xrightarrow{\phantom{xxx}} \quad \text{(I-i)}$$

$$\begin{array}{c} R^{16} \diagdown \hspace{-3pt} \diagup S \diagdown \hspace{-3pt} \diagup R^{17} \\ \| \\ N \diagdown \hspace{-3pt} \diagdown K-D \end{array}$$

$$\underset{(XIX)}{R-N=C=S} + (XVIII) \xrightarrow{\text{ammonia} \atop \text{ammonium salt}} \quad \text{(I-j)}$$

$$\begin{array}{c} R^{18}-NH \diagdown \hspace{-3pt} \diagup S \diagdown \hspace{-3pt} \diagup R^{17} \\ \| \\ N \diagdown \hspace{-3pt} \diagdown K-D, \end{array}$$

wherein $R^{14}$, $R^{15}$, $R^{16}$, $R^{17}$ and $R^{18}$—NH are each independently optional substituents of the thiazole ring.

The cyclization reactions of (XV) with (XVI) and (XVII) with (XVIII) may conveniently be conducted in a suitable reaction inert organic solvent such as, for example, an aromatic hydrocarbon, e.g., benzene and methylbenzene; an aliphatic or alicyclic hydrocarbon, e.g., hexane and cyclohexane; a lower alkanol, e.g., methanol and ethanol; a ketone, e.g., 2-propanone and 4-methyl-2-pentanone; an ether, e.g., 1,4-dioxane, 1,1'-oxybisethane and tetrahydrofuran; an halogenated hydrocarbon, e.g. trichloromethane and the like; N,N-dimethylformamide (DMF); N,N-dimethylacetamide (DMA); and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. Somewhat elevated temperatures may enhance the rate of the reaction.

The cyclization reaction of (XIX) with (XVIII) may conveniently conducted following the same reaction circumstances as used for the preparation of (I-h) and (I-i), provided that the reaction mixture is supplemented with ammonia or an ammonium salt, e.g. ammonium chloride.

The compounds of formula (I), wherein K is a radical of formula —NH—alk—, and wherein Het is optionally substituted 4,5-dihydro-2-thiazolyl ring, may be prepared by condensing a reagent of formula (XX) with an intermediate of formula (VI), wherein X' is S, (VI-a).

$$\underset{(XX)}{\overset{R^{19}}{\underset{|}{W-CH}}-\overset{R^{20}}{\underset{|}{CH}}-NH_2} + \underset{(VI-a)}{S=C=N-Alk-D} \xrightarrow{\phantom{xxx}}$$

$$\begin{array}{c} R^{19} \diagdown \hspace{-3pt} \diagup S \diagdown \hspace{-3pt} \diagup NH-Alk-D \\ \| \\ R^{20} \diagdown \hspace{-3pt} \diagdown N \end{array} \quad \text{(I-k)}$$

The said condensation reaction is conveniently conducted following the same reaction circumstances as described for the preparation of (I-h) or (I-i).

The compounds of formula (I) wherein L is a radical of formula (g), said compounds being represented by the formula (I-l), may also be prepared by reducing an intermediate (XXI) with an appropriate complex metal hydride, e.g. lithium aluminium hydride, in a suitable solvent such as, for example, an ether, e.g. tetrahydrofuran, 1,1'-oxybisethane and the like.

$$\underset{(XXI)}{Het-C_sH_{2s}-Y-Alk'-\overset{O}{\underset{\|}{C}}-D} \xrightarrow{\text{reduction}}$$

$$Het-C_sH_{2s}-Y-Alk'-CH_2-D \quad \text{(I-l)}$$

Alk' having the previously defined meaning of Alk, provided that one methylene function is missing.

The compounds of formula (I) can also be converted into each other following art-known procedures of functional grouptransformation. Some examples will be cited hereinafter.

The compounds of formula (I) having a nitro substituent can be converted into their corresponding amines by stirring and, if desired, heating the starting nitrocompounds in a hydrogen-containing medium in the presence of a suitable amount of an appropriate catalyst such as, for example, platinum-on-charcoal, palladium-on-charcoal, Raney-nickel and the like catalysts. Suitable solvents are, for example, alcohols, e.g., methanol, ethanol and the like.

Halo atoms substituted on aryl groups may be replaced by hydrogen following art-known hydrogenolysis procedures, i.e. by stirring and, if desired, heating the starting compounds in a suitable solvent under hydrogen atmosphere in the presence of an appropriate catalyst, e.g., palladium-on-charcoal and the like catalysts. Said halo atoms may also be replaced by a lower alkyloxy or a lower alkylthio substituent by reacting the starting halo-compound with an appropriate alcohol or thioalcohol or, preferably, an alkali- or earth alkaline metal salt or an appropriate alcohol or thioalcohol in a suitable solvent.

The compounds of formula (I) wherein L is a radical (g) wherein Y is NH can be converted into a compound of formula (I) wherein L is a radical (g) wherein Y is N—CO(lower alkyl) or N—CO($Ar^2$) by reacting the starting amine with an appropriate carboxylic acid or a derivative thereof such as, for example, an acid halide, an acid anhydride and the like.

The compounds of formula (I) wherein L is a radical (g) wherein Y is NH can be converted into a compound of formula (I) wherein L is a radical (g) wherein Y is N—CO(lower alkylamino), N—CO—NH—$Ar^2$, N—CS(lower alkylamino) or N—CS—NH—$Ar^2$ by reacting the starting amine with an appropriate isocyanate or isothiocyanate in a suitable solvent.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

Some intermediates and starting materials in the foregoing preparations are known compounds and others are new. They may be prepared according to art-known methodologies or according to analogous methods thereof. A number of such preparation methods will be described hereinafter in more detail.

The intermediates of formula (III-a) can conveniently be prepared starting from a thiourea derivative of formula

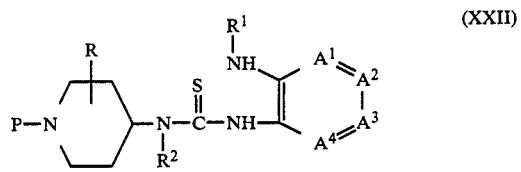

wherein P is an appropriate protective group such as, for example, lower alkyloxycarbonyl, $Ar^2$—$CH_2$—O—CO—, $Ar^2$—$CH_2$— and the like, by a cyclodesulfurization reaction following the same procedure as described hereinabove for the preparation of (I) starting from (IV) and, subsequently eliminating the protective group P in the thus obtained intermediate of formula P-D, (XXIII). The elimination of the protective group P in (XXIII) may generally be carried out following art-known procedures such as, for example, by hydrolysis in alkaline or acidic aqueous medium.

The intermediates of formula (III-b) and (III-c) may be derived from the corresponding intermediates of formula (III-a) by reacting the latter with a suitable reagent following art-known N-alkylating procedures. For example, intermediates of formula (III-b) wherein $Q^{2a}$ represents a radical of formula $H_2N$—$CH_2$—Alk'—, (III-b-1), can also be prepared by reacting an intermediate of formula (III-a) with a nitrile of formula (XXIV) following art-known N-alkylating procedures and subsequently converting the thus obtained nitrile (XXV) into the corresponding amine (III-b-1) following art-known nitrile to amine reducing procedures, e.g., by catalytically hydrogenating procedures and the like.

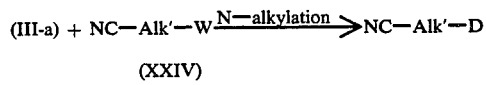

(XXV) $\xrightarrow{\text{nitrile to amine}}_{\text{reduction reaction}}$ $H_2N$—$CH_2$—Alk'—D (III-b-1)

In (XXIV), (XXV) and (III-b-1) Alk' has the same meaning as Alk provided that one methylene function is missing.

The intermediates of formula (III-b) wherein $Q^{2a}$ is Alk-$NH_2$ may be prepared by reacting a reagent (XXVI) with (III-a) following art-known N-alkylating procedures and subsequently converting the thus formed intermediate (XXVII) into the free amine following art-known deprotection procedures.

P—NH—Alk—W + H—D $\xrightarrow{\text{N-alkylation}}$ (XXVI)        (III-a)

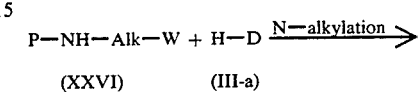

(XXVII)        (III-b-2)

The intermediates of formula (III-b) wherein $Q^{2a}$ represents a radical of formula HY'—$CH_2$—$CH_2$—, (III-b-3), may also be prepared by the reaction of (III-a) with a reagent of formula (XXVIII) by stirring and, if desired, heating the reactants together in a suitable solvent.

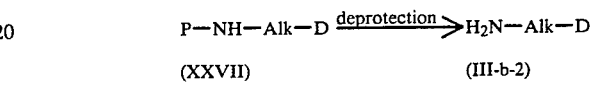

(XXVIII)        (III-b-3)

The intermediates of formula (III-b) wherein $Q^{2a}$ is a radical of formula HX—Alk—, (III-d), may be converted into an intermediate of formula (III-c) by converting the function Y'H into an appropriate leaving group, e.g., where Y' is O, by converting a hydroxy function into a chloro atom, with thionyl chloride, phosphoryl chloride and the like.

The intermediates of formula (III-b-2) may also be derived from an appropriate corresponding carbonyl-oxidated form by reacting said carbonyl-oxidated form with hydroxylamine and reducing the thus obtained oxime following art-known methods, e.g., catalytic hydrogenation and the like reducing methods.

During one of the reactions the intermediate wherein $R^1$ and/or $R^2$ and/or $R^3$ and/or $R^4$ is hydrogen may be converted into the corresponding intermediates wherein $R^1$ and/or $R^2$ and/or $R^3$ and/or $R^4$ is other than hydrogen following art-known N-alkylating, N-acylating or reductive N-alkylating procedures.

The intermediates of formula (XXII) and the intermediates of formula (XXII) wherein $R^2$ is hydrogen, (XXII-a) may be prepared by reacting a piperidine of formula (XXIX-a) or (XXIX-b) with an aromatic reagent of formula (XXX-a) or (XXX-b).

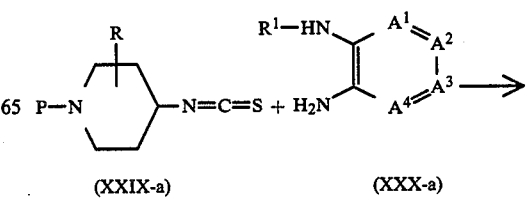

(XXIX-a)        (XXX-a)

-continued

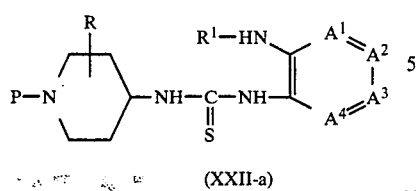

(XXII-a)

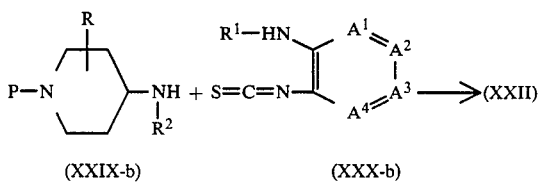

(XXIX-b)      (XXX-b)

The intermediates of formula (XI) wherein K is a radical of formula (i) wherein s is 0, a radical of formula (j) wherein s=0 and Y is other than a direct bond or a radical of formula (k) wherein s=0 and Z is other than a direct bond, said K being represented by K' and said intermediates by the formula (XI-a), can be prepared by reacting a piperidine of formula (III-b), wherein $Q^{2a}$ is a radical —K'H, said piperidine being represented by the formula (III-b-4), with an intermediate of formula (XXXI).

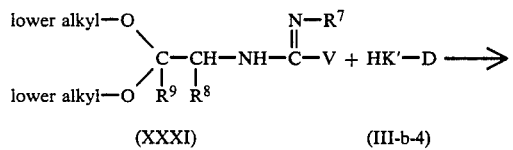

(XXXI)      (III-b-4)

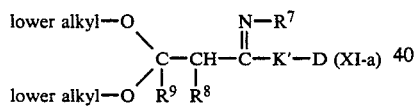

wherein V represents an appropriate leaving group, such as, for example, lower alkylthio, lower alkyloxy, halo and the like.

The intermediates of formula (XXXI) may be prepared following art-known procedures such as, for example, where V is lower alkylthio, by alkylating an appropriate thiourea derivative with an appropriate alkyl halide.

The intermediates of formula (XII), wherein K is —NH—Alk— said intermediates being represented by the formula (XII-a), can conveniently be prepared by reacting an appropriate aryl derivative of formula (XXXII) with an intermediate of formula (VI) wherein X' is S, (VI-a).

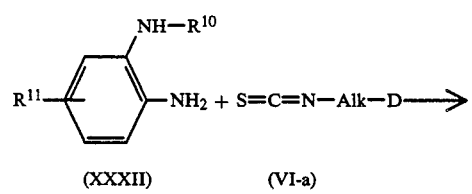

(XXXII)      (VI-a)

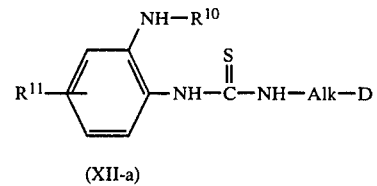

(XII-a)

The intermediates of formula (XIV) may be prepared by N-alkylating an intermediate of formula (III-a) with a nitrile of formula NC—K—W following art-known N-alkylating procedures.

Additionally, the intermediates of formula (XIV) wherein K is a radical of formula —NH—Alk—, said intermediate being represented by the formula (XIV-a) can also be prepared by reacting a cyanogen halide of formula (XXXIII) with an intermediate of formula (III-b) wherein $Q^{2a}$ represents a radical of formula $H_2N$—Alk—, said intermediate being represented by the formula (III-b-2).

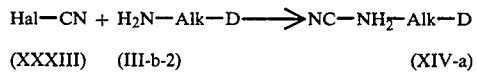

(XXXIII)    (III-b-2)      (XIV-a)

The intermediates of formula (XVI) wherein K is a radical of formula —NH—Alk— can be prepared by reacting an intermediate (VI-a) with ammonia or an ammonium salt, e.g. ammonium chloride and the like, in the presence of a suitable solvent.

The intermediates of formula (XVIII), wherein W is a halogen radical, said intermediates being represented by formula (XVIII-a), can be prepared by halogenating an intermediate (XXXIV), which can be prepared by N-alkylating (III-a) with a reagent of formula $R^{17}$—$CH_2$—CO—K—W.

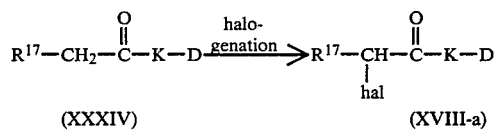

(XXXIV)      (XVIII-a)

The intermediates of formula (XXI) can be prepared by N-acylating an intermediate (III-a) with an appropriate reagent of formula Het—$C_sH_{2s}$—Y—Alk'—C-O—W.

From formula (I) it is evident that the compounds of this invention may have several asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, 511 (1966).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

The following examples are intended to illustrate and not to limit the scope of the present invention. Unless otherwise stated all parts therein are by weight.

EXAMPLES (A) Preparation of Intermediates

EXAMPLE 1

To a stirred and heated (60° C.) solution of 41.3 parts of 1H-benzimidazol-2-amine in 162 parts of N,N-dimethylformamide (DMF) were added portionwise during a 40 minutes period 12 parts of sodium hydride dispersion 60%. Upon completion, stirring at 60° C. was continued for 30 minutes. After cooling to 40° C., there was added dropwise during 25 minutes a solution of 50 parts of 1-(chloromethyl)-3-fluorobenzene in 9 parts of DMF and 36 parts of methylbenzene. After the addition was complete, the whole was stirred for 1.50 hours at 50°–65° C. The reaction mixture was cooled and water was added. The solid product was filtered off and crystallized from a mixture of 2,2′-oxybispropane, tetrahydrofuran and methanol. The product was filtered off and recrystallized from methylbenzene, yielding 34.8 parts of 1-[(3-fluorophenyl)methyl]-1H-benzimidazol-2-amine; mp. 188.1° C. (1).

In a similar manner there was also prepared: 2-chloro-1-(4-fluorophenylmethyl-1H-benzimidazole (2).

EXAMPLE 2

A mixture of 20 parts of 1-[(3-fluorophenyl)methyl]-1H-benzimidazol-2-amine, 495 parts of methylbenzene and 1 part of 4-methylbenzenesulfonic acid was stirred and refluxed for 1.50 hours under nitrogen atmosphere and using a water separator. Then there was added dropwise a solution of 15.4 parts of ethyl 4-oxo-1-piperidinecarboxylate in 45 parts of methylbenzene and stirring at reflux was continued for 23 hours. The mixture was cooled, filtered and the filtrate was evaporated. To the oily residue were added 120 parts of methanol. After cooling to 3° C., there were added portionwise 3.04 parts of sodium borohydride. Upon completion, the whole was stirred for 2.15 hours at 18° C. and for 65.40 hours at room temperature. The residue mixture was diluted with water and the product was extracted with tricholormethane. The extract was dried, filtered and evaporated, yielding 17.2 parts (60%) of ethyl 4-[[1-[(3-fluorophenyl)methyl]-1H-benzimidazole-1-yl]amino]-1-piperidinecarboxylate; mp. 184.6° C. (3).

EXAMPLE 3

To a stirred and cooled mixture of 4 parts of sodium hydroxide in 60 parts of water were added successively 7.9 parts of carbon disulfide and 17.2 parts of ethyl 4-amino-1-piperidinecarboxylate at a temperature below 10° C. Stirring was continued for 30 minutes at this temperature. Then there were added dropwise 10.9 parts of ethyl carbonochloridate (exothermic reaction: temp. rises to about 35° C.). Upon completion, stirring was continued for 2 hours at 60° C. The reaction mixture was cooled and the product was extracted with methylbenzene. The extract was dried, filtered and evaporated, yielding 22 parts (100%) of ethyl 4-isothiocyanato-1-piperidinecarboxylate (4).

EXAMPLE 4

A mixture of 90 parts of 4-chloro-3-nitropyridine, 71 parts of 4-fluorobenzenemethanamine, 63 parts of sodium carbonate and 900 parts of N,N-dimethylacetamide (DMA) was stirred for 1 hour at 50° C. Water was added and the product was extracted with 4-methyl-2-pentanone. The extract was dried, filtered and evaporated. The residue was crystallized from acetonitrile. The product was filtered off and dried, yielding 106 parts (75%) of N-[(4-fluorophenyl)methyl]-3-nitro-4-pyridinamine; mp. 136.8° C. (5).

In a similar manner there were also prepared:

$N^3$-[(4-fluorophenyl)methyl]-2,3-pyridinediamine (6);

N-[(4-fluorophenyl)methyl]-4-nitro-3-pyridinamine, 1-oxide (7);

N-(2-nitrophenyl)-2-furanmethanamine; mp. 85.6° C. (8);

N-(3-nitro-2-pyridinyl)-2-pyridinemethanamine; mp. 113.6° C. (9);

2-nitro-N-(2-thienylmethyl)benzenamine (10);

3-nitro-N-(2-thienylmethyl)-2-pyridinamine; mp. 100° C. (11);

4-fluoro-N-(4-methoxy-2-nitrophenyl)benzenemethanamine (12);

4-fluoro-N-(4-methyl-2-nitrophenyl)benzenemethanamine; mp. 99.9° C. (13);

2,6-difluoro-N-(2-nitrophenyl)benzenemethanamine (14); and 4-fluoro-N-(5-methoxy-2-nitrophenyl)benzenemethanamine (15).

EXAMPLE 5

To a stirred and cooled (0° C.) solution of 8.7 parts of N-[(4-fluorophenyl)methyl]-4-nitro-3-pyridinamine, 1-oxide and 150 parts of trichloromethane was added dropwise a solution of 10.2 parts of phosphor trichloride in 75 parts of trichloromethane. Upon completion, the mixture was allowed to reach room temperature and stirring was continued for 1 hour at reflux temperature. The reaction mixture was cooled and the solvent was evaporated. The residue was stirred in trichloromethane. The product was filtered off and dried, yielding 9 parts of N-[(4-fluorophenyl)methyl]-4-nitro-3-pyridinamine monohydrochloride (16).

EXAMPLE 6

A mixture of 125 parts of 3-nitro-N-(2-thienylmethyl)-2-pyridinamine and 560 parts of methanol saturated with ammonia was hydrogenated at normal pressure and at room temperature with 10 parts of platinum-on-charcoal catalyst 5%. After the calculated amount of hydrogen was taken up, the catalyst was filtered off and the filtrate was evaporated. The residue was stirred overnight in 1,1′-oxybisethane. The product was filtered off and dried in vacuo at 40° C., yielding 77 parts (70.8%) of $N^2$-(2-thienylmethyl)-2,3-pyridine-diamine; mp. 92.1° C. (17).

In a similar manner there were also prepared:

$N^4$-[(4-fluorophenyl)methyl]-3,4-pyridinediamine; mp. 163.7° C. (18);

N-(2-furanylmethyl)-1,2-benzenediamine (19);

N³-[(4-fluorophenyl)methyl]-3,4-pyridinediamine monohydrochloride; mp. 208.9° C. (20);

N²-(2-pyridinylmethyl)-2,3-pyridinediamine; mp. 134.9° C. (21);

N²-(2-furanylmethyl)-2,3-pyridinediamine (22);

N¹-(2-thienylmethyl)-1,2-benzenediamine (23);

N¹-[(4-fluorophenyl)methyl]-4-methoxy-1,2-benzenediamine (24);

N¹-[(4-fluorophenyl)methyl]-4-methyl-1,2-benzenediamine (25);

N¹-[(2,6-difluorophenyl)methyl]-1,2-benzenediamine (26);

N²-[(4-fluorophenyl)methyl]-4-methoxy-1,2-benzenediamine (27);

EXAMPLE 7

A mixture of 54 parts of ethyl 4-isothiocyanato-1-piperidinecarboxylate, 48 parts of N²-(2-furanylmethyl)-2,3-pyridinediamine and 450 parts of tetrahydrofuran was stirred and refluxed overnight. The reaction mixture was evaporated and the residue was crystallized from a mixture of 2-propanone and 2,2'-oxybispropane. The product was filtered off and dried, yielding 76 parts (75%) of ethyl 4-[[[2-[(2-furanylmethyl)amino]-3-pyridinyl]aminothioxomethyl]amino]-1-piperidinecarboxylate; mp. 132.7° C. (28).

Following the same procedure and using the equivalent amounts of the appropriate starting materials, there were also prepared:

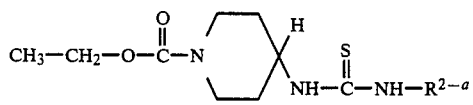

| No. | R²⁻ᵃ | mp. °C. |
|---|---|---|
| 29 | 2-[(2-furanylmethyl)amino]phenyl | — |
| 30 | 3-[[(4-fluorophenyl)methyl]amino]-2-pyridinyl | — |
| 31 | 4-[[(4-fluorophenyl)methyl]amino]-3-pyridinyl | 166 |
| 32 | 3-[[(4-fluorophenyl)methyl]amino]-4-pyridinyl | — |
| 33 | 2-[(2-pyridinylmethyl)amino]-3-pyridinyl | — |
| 34 | 2-[(2-thienylmethyl)amino]phenyl | — |
| 35 | 2-[(2-thienylmethyl)amino]-3-pyridinyl | — |
| 36 | 2-[[(4-methoxyphenyl)methyl]amino]phenyl | — |
| 37 | 2-[[(4-fluorophenyl)methyl]amino]-5-methylphenyl | — |
| 38 | 2-[[(2,6-difluorophenyl)methyl]amino]phenyl | — |
| 39 | 2-[[(4-fluorophenyl)methyl]amino]-4-methoxyphenyl | — |
| 40 | 2-[[(4-fluorophenyl)methyl]amino]-5-methoxyphenyl | — |

EXAMPLE 8

A mixture of 28 parts of ethyl 4-[[(2-aminophenyl)aminothioxomethyl]amino]-1-piperidinecarboxylate, 112 parts of iodomethane and 240 parts of ethanol was stirred and refluxed for 8 hours. The reaction mixture was evaporated and the residue was taken up in water. The whole was alkalized with ammonium hydroxide and the product was extracted with dichloromethane. The extract was dried, filtered and evaporated. The residue was crystallized from a mixture of 2-propanol and 2,2'-oxybispropane. The product was filtered off and dried, yielding 7 parts (28%) of ethyl 4-(1H-benzimidazol-2-yl-amino)-1-piperidinecarboxylate (41).

EXAMPLE 9

A mixture of 74 parts of ethyl 4-[[[2-[(2-furanylmethyl)amino]-3-pyridinyl]aminothioxomethyl]amino]-1-piperidinecarboxylate, 96 parts of mercury(II)oxide, 0.1 parts of sulfur and 800 parts of ethanol was stirred and refluxed for 3 hours. The reaction mixture was filtered over Hyflo and the filtrate was evaporated. The residue was crystallized from acetonitrile, yielding 52.5 parts (79%) of ethyl 4-[[3-(2-furanylmethyl)-3H-imidazo[4,5-b]pyridin-2-yl]amino]-1-piperidinecarboxylate; mp. 149.2° C. (42).

In a similar manner there were also prepared:

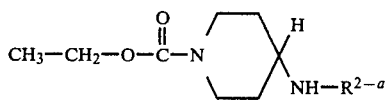

| No. | R²⁻ᵃ | mp. °C. |
|---|---|---|
| 43 | 1-[(4-fluorophenyl)methyl]-1H—imidazo[4,5-b]pyridin-2-yl | 212.5 |
| 44 | 1-(2-furanylmethyl)-1H—benzimidazol-2-yl | 135.8 |
| 45 | 1-[(4-fluorophenyl)methyl]-1H—imidazo[4,5-c]pyridin-2-yl* | — |
| 46 | 3-[(4-fluorophenyl)methyl]-3H—imidazo[4,5-c]pyridin-2-yl* | 168.6 |
| 47 | 3-(2-pyridinylmethyl)-3H—imidazo[4,5-b]pyridin-2-yl | 141.3 |
| 48 | 1-(2-thienylmethyl)-1H—benzimidazol-2-yl | 142.7 |
| 49 | 3-(2-thienylmethyl)-3H—imidazo[4,5-b]pyridin-2-yl | — |
| 50 | 1-[(4-methoxyphenyl)methyl]-1H—benzimidazol-2-yl | 157.1 |
| 51 | 1-[(4-fluorophenyl)methyl]-5-methyl-1H—benzimidazol-2-yl | 202.0 |
| 52 | 1-[(2,6-difluorophenyl)methyl]1H—benzimidazol-2-yl | 140.0 |
| 53 | 1-[(4-fluorophenyl)methyl]-6-methoxy-1H—benzimidazol-2-yl | — |
| 54 | 1-[(4-fluorophenyl)methyl]-5-methoxy-1H—benzimidazol-2-yl | — |

*dihydrochloride.monohydrate salt

EXAMPLE 10

A mixture of 57.5 parts of ethyl 4-(1H-benzimidazol-2-ylamino)-1-piperidinecarboxylate, 33 parts of 2-(chloromethyl)pyridine hydrochloride, 43 parts of sodium carbonate, 0.1 parts of potassium iodide and 630 parts of DMF was stirred and heated overnight at 70° C. The reaction mixture was cooled and poured into water. The product was extracted with 4-methyl-2-pentanone. The extract was dried, filtered and evaporated. The residue was purified by column chromatography over silica gel using a mixture of trichloromethane and methanol (96:4 by volume) as eluent. The pure fractions were collected and the eluent was evaporated. The residue was crystallized from 4-methyl-2-pentanone, yielding 30 parts (40%) of ethyl 4-[[1-[(2-pyridinyl)methyl]-1H-benzimidazol-2-yl]amino]-1-piperidinecarboxylate; mp. 161.5° C. (55).

Following the same procedure and using equivalent amounts of the appropriate starting materials, there were also prepared:

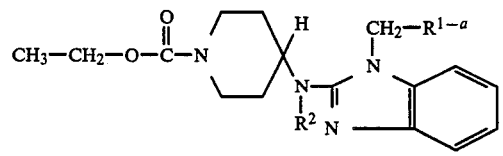

| No. | R¹⁻ᵃ | R² | mp. °C. |
|---|---|---|---|
| 56 | (3-pyridinyl) | H | 191.4 |
| 57 | (4-thiazolyl) | H | 156.2 |
| 58 | (4-fluorophenyl) | CH₃ | — |
| 59 | (3,4-dimethylphenyl) | H | — |
| 60 | (3-chlorophenyl) | H | — |

-continued

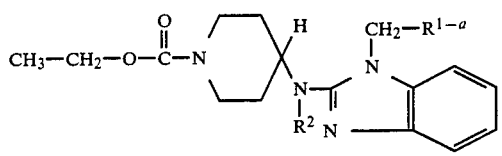

| No. | R$^{1-a}$ | R$^2$ | mp. °C. |
|---|---|---|---|
| 61 | (2-methylphenyl) | H | — |
| 62 | (3-methylphenyl) | H | — |
| 63 | (2-iodophenyl) | H | — |
| 64 | (2-bromo-4-fluorophenyl) | H | — |
| 65 | (4-fluorophenyl) | H | 180.8 |

EXAMPLE 11

A mixture of 30 parts of ethyl 4-[[1-[(2-pyridinyl)methyl]-1H-benzimidazol-2-yl]amino]-1-piperidinecarboxylate and 300 parts of a hydrobromic acid solution 48% in water was stirred and heated for 3 hours at 80° C. The reaction mixture was evaporated and the residue was crystallized from methanol, yielding 41 parts (93.2%) of N-(4-piperidinyl)-1-[(2-pyridinyl)methyl]-1H-benzimidazol-2-amine trihydrobromide; mp. 295.9° C. (66).

Following the same procedure and using equivalent amounts of the appropriate starting materials, there were also prepared:

1,1'-oxybisethane. The product was filtered off and dried, yielding 34 parts (85%) of 3-(2-furanylmethyl)-N-(4-piperidinyl)-3H-imidazo-[4,5-b]pyridin-2-amine; mp. 159.0° C. (81).

Following the same procedure and using equivalent amounts of the appropriate starting materials, there were also prepared:

1-(2-furanylmethyl)-N-(1-piperidinyl)-1H-benzimidazol-2-amine; mp. 211.0° C. (82);

N-(4-piperidinyl)-1-(2-thienylmethyl)-1H-benzimidazol-2amine (83);

N-4-piperidinyl)-3-(2-thienylmethyl)-3H-imidazo[4,5-b]pyridin-2-amine; mp. 189.6°–193.5° C. (84);

1-[(4-methoxyphenyl)methyl]-N-(4-piperidinyl)-1H-benzimidazol-2-amine; mp. 178.1° C. (85);

1-[(4-fluorophenyl)methyl]-N-methyl-N-(4-piperidinyl)-1H-benzimidazol-2-amine dihydrochloride monohydrate; mp. 222.2° C. (86);

1-[(4-fluorophenyl)methyl]-5-methoxy-N-(4-piperidinyl)-1H-benzimidazol-2-amine (87);

1-[(4-fluorophenyl)methyl]-6-methoxy-N-(4-piperidinyl)-1H-benzimidazol-2-amine (88); and 1-[(4-fluorophenyl)methyl]-5-methyl-N-(4-piperidinyl)-1H-benzimidazol-2-amine (89).

EXAMPLE 13

A mixture of 11 parts of 4-chlorobutanenitrile, 48.5 parts of 1-(4-fluorophenylmethyl)-N-(4-piperidinyl)-1H-benzimidazol-2-amine dihydrobromide, 30 parts of

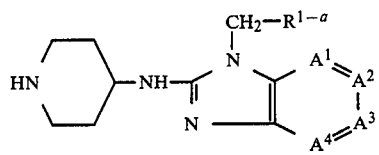

| No. | R$^{1-a}$ | A$^1$=A$^2$—A$^3$=A$^4$ | base or salt form | mp. in °C. |
|---|---|---|---|---|
| 67 | 3-fluorophenyl | CH=CH—CH=CH | base | 218.4 |
| 68 | 3-pyridinyl | CH=CH—CH=CH | 3HBr | +260 |
| 69 | 4-fluorophenyl | CH=CH—CH=N | 2HBr | +300.6 |
| 70 | 4-fluorophenyl | CH=CH—N=CH | 2HBr | 279.4 |
| 71 | 2-pyridinyl | N=CH—CH=CH | 3HBr | 265.5 |
| 72 | 4-fluorophenyl | CH=N—CH=CH | 2HBr.H$_2$O | 291.6 |
| 73 | 4-thiazolyl | CH=CH—CH=CH | 2HBr.H$_2$O | 223.5 |
| 74 | 3-chlorophenyl | CH=CH—CH=CH | 2HBr | 262.2 |
| 75 | 2-methylphenyl | CH=CH—CH=CH | 2HBr | — |
| 76 | 3-methylphenyl | CH=CH—CH=CH | 2HBr | — |
| 77 | 2-bromo-4-fluorophenyl | CH=CH—CH=CH | 2HBr | — |
| 78 | 2-iodophenyl | CH=CH—CH=CH | 2HBr.H$_2$O | 265.2 |
| 79 | 4-fluorophenyl | CH=CH—CH=CH | 2HBr | 290.2 |
| 80 | 2,6-difluorophenyl | CH=CH—CH=CH | 2HBr | 295.5 |

EXAMPLE 12

A mixture of 50 parts of ethyl 4-[[3-(2-furanylmethyl)-3H-imidazo-[4,5-b]pyridin-2-yl]amino]-1-piperidinecarboxylate, 50 parts of potassium hydroxide, 400 parts of 2-propanol and 20 drops of water was stirred and refluxed for about 5 hours. The reaction mixture was evaporated and water was added to the residue. The product was extracted twice with 4-methyl-2-pentanone. The combined extracts were dried, filtered and evaporated. The solid residue was stirred in sodium carbonate and 270 parts of DMF was stirred and heated overnight at 70° C. The reaction mixture was poured into water and the product was extracted with trichloromethane. The extract was dried, filtered and evaporated. The residue was crystallized twice from a mixture of 4-methyl-2-pentanone and 2,2'-oxybispropane, yielding 2.2 parts (80%) of 4-[[1-[(4-fluorophenyl)methyl]-1H-benzimidazol-2-yl]amino]-1-piperidinebutanenitrile; mp. 130.5° C. (90).

In a similar manner there were also prepared:

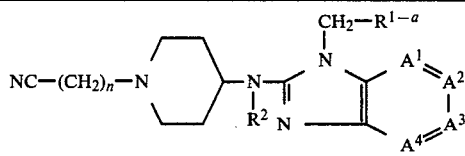

| No. | n | $R^2$ | $R^{1-a}$ | $A^1=A^2-A^3=A^4$ | base or salt form | mp. in °C. |
|---|---|---|---|---|---|---|
| 91 | 1 | H | 4-fluorophenyl | —N=CH—CH=CH— | — | 183.7 |
| 92 | 1 | H | 2-pyridinyl | —CH=CH—CH=CH— | — | 152.6 |
| 93 | 1 | H | 4-fluorophenyl | —CH=CH—CH=CH— 5(and 6)-F | — | 176.7 |
| 94 | 1 | H | 3-pyridinyl | —CH=CH—CH=CH— | ½ H$_2$O | 204.5 |
| 95 | 1 | H | 4-fluorophenyl | —CH=CH—CH=N— | ½ H$_2$O | 173.9 |
| 96 | 1 | H | 2-furanyl | —CH=CH—CH=CH— | — | 194.4 |
| 97 | 1 | H | 4-fluorophenyl | —CH=CH—N=CH— | H$_2$O | 188.5 |
| 98 | 1 | H | 2-pyridinyl | —N=CH—CH=CH— | — | 170.0 |
| 99 | 1 | H | 2-furanyl | —N=CH—CH=CH— | — | 157.0 |
| 100 | 1 | H | 2-thienyl | —CH=CH—CH=CH— | — | 191.7 |
| 101 | 1 | H | 4-fluorophenyl | —CH=N—CH=CH— | — | — |
| 102 | 4 | H | 4-fluorophenyl | —CH=CH—CH=CH— | — | 144.0 |
| 103 | 1 | H | 2-thienyl | —N=CH—CH=CH— | — | 157.8 |
| 104 | 2 | H | 4-fluorophenyl | —N=CH—CH=CH— | — | 199.8 |
| 105 | 1 | H | H | —CH=CH—CH=CH— | — | 212.3 |
| 106 | 1 | H | phenyl | —CH=CH—CH=CH— | — | 180.4 |
| 107 | 1 | H | 4-methylphenyl | —CH=CH—CH=CH— | — | 155.2 |
| 108 | 1 | H | 4-chlorophenyl | —CH=CH—CH=CH— | — | 180.4 |
| 109 | 1 | H | 4-methoxyphenyl | —CH=CH—CH=CH— | — | 169.9 |
| 110 | 1 | CH$_3$ | 4-fluorophenyl | —CH=CH—CH=CH— | — | 157.4 |
| 111 | 1 | H | 3,4-dimethoxyphenyl | —CH=CH—CH=CH— | — | 165.0 |
| 112 | 1 | H | 3-chlorophenyl | —CH=CH—CH=CH— | — | — |
| 113 | 1 | H | 2-methylphenyl | —CH=CH—CH=CH— | — | 180.5 |
| 114 | 1 | H | 3-methylphenyl | —CH=CH—CH=CH— | — | — |
| 115 | 1 | H | 2-fluorophenyl | —CH=CH—CH=CH— | — | 179.3 |
| 116 | 1 | H | 4-fluorophenyl | —CH=CH—CH=CH— 5-methyl | — | 203.0 |
| 117 | 1 | H | 2,6-difluorophenyl | —CH=CH—CH=CH— | — | 197.4 |
| 118 | 1 | H | 4-fluorophenyl | —CH=CH—CH=CH— 5-methoxy | — | 174.8 |
| 119 | 1 | H | 4-fluorophenyl | —CH=CH—CH=CH— 6-methoxy | — | 222.0 |
| 120 | 1 | H | 3-fluorophenyl | —CH=CH—CH=CH— | — | 195.5 |

In a similar manner there were also prepared:

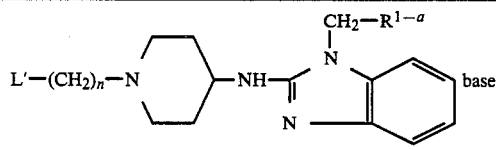

| No. | L' | n | $R^{1-a}$ | mp. in °C. |
|---|---|---|---|---|
| 121 | acetyl | 1 | 4-fluorophenyl | — |
| 122 | ethoxycarbonylamino | 2 | 4-thiazolyl | — |
| 123 | ethoxycarbonylamino | 2 | 2-bromo-4-fluorophenyl | — |
| 124 | ethoxycarbonylamino | 2 | 2-iodophenyl | — |
| 125 | ethoxycarbonylamino | 2 | 4-nitrophenyl | — |

In a similar manner there were also prepared:
(cis+trans)-4-[[1-[(4-fluorophenyl)methyl]-1H-benzimidazol-2-yl]-amino]-3-methyl-1-piperidineacetonitrile; mp. 150.1° C. (126);
4-[(1H-benzimidazol-2-yl)amino]-1-piperidineacetonitrile; mp. 226° C. (127); and
4-[(1-phenyl-1H-benzimidazol-2-yl)amino]-1-piperidineacetonitrile (128).

EXAMPLE 14

To a stirred mixture of 3.14 parts of 3-furancarboxylic acid, 6 parts of N,N-diethylethanamine and 390 parts of dichloromethane were added 7.2 parts of 2-chloro-1-methylpyridinium iodide. After stirring for 10 minutes at room temperature, 7 parts of 4-[(1H-benzimidazol-2-yl)amino]-1-piperidineacetonitrile were added and the whole was stirred for 1 hour at room temperature. The reaction mixture was washed with water. The organic phase was dried, filtered and evaporated. The residue was crystallized from acetonitrile, yielding 7 parts (74%) of 4-[[1-(3-furanylcarbonyl)-1H-benzimidazol-2-yl]amino]-1-piperidineacetonitrile (129).

To 180 parts of tetrahydrofuran were added carefully 2.4 parts of lithium aluminum hydride under nitrogen atmosphere. Then there was added dropwise a solution of 7 parts of 4-[[1-(3-furanyl-carbonyl)-1H-benzimidazol-2-yl]amino]-1-piperidineacetonitrile in tetrahydrofuran: temp. rose to 50° C. Upon completion, stirring was continued overnight at reflux temperature. The reaction mixture was cooled in an ice bath and decomposed by the successive additions of 3 parts of water, 9 parts of a sodium hydroxide solution 15% and 9 parts of water. The whole was filtered over Hyflo and the filtrate was evaporated. The residue was purified by filtration over silica gel using a mixture of trichloromethane and methanol (80:20 by volume) saturated with ammonia, as eluent. The pure fractions were collected and the eluent was evaporated. The residue was crystallized from acetonitrile, yielding 3.6 parts (69.5%) of N-[1-(2-amino-ethyl)-4-piperidinyl]-1H-benzimidazol-2-amine; mp. 99.8° C. (130).

EXAMPLE 15

To a stirred mixture of 2.5 parts of lithium aluminum hydride and 225 parts of tetrahydrofuran was added dropwise a solution of 13 parts of 4-[[1-(2-thienylmethyl)-1H-benzimidazol-2-yl]amino]-1-piperidineacetonitrile in tetrahydrofuran under nitrogen atmosphere. Upon completion, stirring was continued for 3 hours at reflux. The reaction mixture was cooled in an ice bath and decomposed by the successive additions of 2.5 parts of water, 7.5 parts of sodium hydroxide solution 15% and 7.5 parts of water. The whole was filtered over Hyflo and the filtrate was evaporated. The residue was crystallized from acetonitrile, yielding 9.5 parts (72%) of N-[1-(2-aminoethyl)-4-piperidinyl]-1-(2-thienylmethyl)-1H-benzimidazol-2-amine; mp. 137.1° C. (131).

Following the same procedure and using equivalent amounts of the appropriate starting materials, there was also prepared: N-[1-(2-aminoethyl)-4-piperidinyl]-3-(2-thienylmethyl)-3H-imidazo[4,5-b]pyridin-2-amine; mp. 138.5° C. (132).

EXAMPLE 16

A mixture of 12 parts of 4-[[1-[(4-fluorophenyl)methyl]-1H-imidazo[4,5-b]pyridin-2-yl]amino]-1-piperidineacetonitrile and 200 parts of methanol saturated with ammonia was hydrogenated at normal pressure and at room temperature with 2 parts of Raney-nickel catalyst. After the calculated amount of hydrogen was taken up, the catalyst was filtered off and the filtrate was evaporated. The residue was crystallized from acetonitrile, yielding 10 parts (78%) of N-[1-(2-aminoethyl)-4-piperidinyl]-1-[(4-fluorophenyl)methyl]-1H-imidazo[4,5-b]pyridin-2-amine monohydrate; mp. 116.9° C. (133)).

Following the same procedure and using equivalent amounts of the appropriate starting materials, there were also prepared:

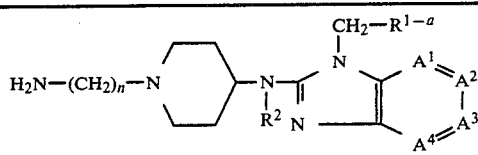

| No. | n | $R^2$ | $R^{1-a}$ | $A^1=A^2-A^3=A^4$ | base or salt | mp. in °C. |
|---|---|---|---|---|---|---|
| 134 | 4 | H | 4-fluorophenyl | —CH=CH—CH=CH— | — | — |
| 135 | 2 | H | 4-fluorophenyl | —N=CH—CH=CH— | — | 174.5 |
| 136 | 2 | H | 2-pyridinyl | —CH=CH—CH=CH— | — | 145.1 |
| 137 | 2 | H | 4-fluorophenyl | —CH=CH—CH=CH— 5(and 6)-F | — | 171.0 |
| 138 | 2 | H | 3-pyridinyl | —CH=CH—CH=CH— | — | 150.7 |
| 139 | 2 | H | 2-furanyl | —CH=CH—CH=CH— | — | 163.1 |
| 140 | 2 | H | 4-fluorophenyl | —CH=CH—N=CH— | $H_2O$ | 185.0 |
| 141 | 2 | H | 2-pyridinyl | —N=CH—CH=CH— | — | 151.1 |
| 142* | 2 | H | 2-furanyl | —N=CH—CH=CH— | $H_2O$ | 182.0 |
| 143 | 2 | H | 4-fluorophenyl | —CH=N—CH=CH— | — | — |
| 144 | 5 | H | 4-fluorophenyl | —CH=CH—CH=CH— | — | 172.9 |
| 145 | 3 | H | 4-fluorophenyl | —N=CH—CH=CH— | — | 167.8 |
| 146 | 2 | H | H | —CH=CH—CH=CH— | — | 199.0 |
| 147 | 2 | H | phenyl | —CH=CH—CH=CH— | — | 131.6 |
| 148 | 2 | H | 4-chlorophenyl | —CH=CH—CH=CH— | — | 143.4 |
| 149* | 2 | H | 4-methylphenyl | —CH=CH—CH=CH— | — | 260.1 |
| 150 | 2 | H | 4-methoxyphenyl | —CH=CH—CH=CH— | — | 129.8 |
| 151 | 2 | $CH_3$ | 4-fluorophenyl | —CH=CH—CH=CH— | — | — |
| 152 | 2 | H | 3,4-dimethylphenyl | —CH=CH—CH=CH— | — | — |
| 153 | 2 | H | 3-chlorophenyl | —CH=CH—CH=CH— | — | — |
| 154 | 2 | H | 2-methylphenyl | —CH=CH—CH=CH— | — | — |
| 155 | 2 | H | 3-methylphenyl | —CH=CH—CH=CH— | — | — |
| 156 | 2 | H | 2-fluorophenyl | —CH=CH—CH=CH— | — | — |
| 157 | 2 | H | 3-fluorophenyl | —CH=CH—CH=CH— | — | 144.7 |
| 158 | 2 | H | 4-fluorophenyl | —CH=CH—CH=CH— 5-methyl | — | 155.7 |
| 159 | 2 | H | 2,6-difluorophenyl | —CH=CH—CH=CH— | — | — |
| 160 | 2 | H | 4-fluorophenyl | —CH=CH—CH=CH— 5-methoxy | — | — |
| 161 | 2 | H | 4-fluorophenyl | —CH=CH—CH=CH— 6-methoxy | — | — |

*(E)—2-butenedioate (1:3) salt

In a similar manner there was also prepared:
(cis+trans)-N-[1-(2-aminoethyl)-3-methyl-4-piperidinyl]-1-[(4-fluorophenyl)methyl]-1H-benzimidazol-2-amine; mp. 132.2° C. (162); and N-[1-(2-aminoethyl)-4-piperidinyl]-1-phenyl-1H-benzimidazol-2-amine (163).

EXAMPLE 17

A mixture of 33 parts of ethyl [2-[4-[[1-[(2-bromo-4-fluorophenyl)methyl]-1H-benzimidazol-2-yl]amino]-1-piperidinyl]ethyl]carbamate and 750 parts of a hydrobromic acid solution 48% in water was stirred overnight at 80° C. The reaction mixture was evaporated. The residue was crystallized from ethanol. The product was filtered off and dried, yielding 22.5 parts (65%) of N-[1-(2-aminoethyl)-4-piperidinyl]-1-[(2-bromo-4-fluorophenyl)methyl]-1H-benzimidazol-2-amine trihydrobromide.monohydrate; mp. 224.7° C. (164).

In a similar manner there were also prepared:
N-[1-[(4-fluorophenyl)methyl]-1H-benzimidazol-2-yl]-[1,4'-bipiperidine]-4-amine (165);

N-[1-(2-aminoethyl)-4-piperidinyl]-1-(4-thiazolylmethyl)-1H-benzimidazol-2-amine trihydrobromide (166);

N-[1-(2-aminoethyl)-4-piperidinyl]-1-[(2-iodophenyl)methyl]-1H-benzimidazol-2-amine trihydrobromide.-monohydrate; mp. 261.5° C. (167);

N-[1-(2-aminoethyl)-4-piperidinyl]-1-[(4-aminophenyl)methyl]-1H-benzimidazol-2-amine trihydrobromide (168); and N-[1-(2-aminoethyl)-4-piperidinyl]-1-[(4-nitrophenyl)methyl]-1H-benzimidazol-2-aminetrihydrobromide (169).

EXAMPLE 18

A mixture of 24 parts of ethyl [2-[4-[[1-[(4-nitrophenyl)methyl]-1H-benzimidazol-2-yl]amino]-1-piperidinyl]-ethyl]carbamate, 1 part of a solution of thiophene in methanol 4% and 250 parts of 2-methoxyethanol was hydrogenated at normal pressure and at 50° C. with 3 parts of palladium-on-charcoal catalyst 10%. After the calculated amount of hydrogen was taken up, the catalyst was filtered off and the filtrate was evaporated, yielding 22.5 parts (100%) of ethyl [2-[4-[[1-[(4-aminophenyl)methyl]-1H-benzimidazol-2-yl]amino]-1-piperidinyl]ethyl]carbamate as a residue (170).

EXAMPLE 19

To 2 parts of a solution of 2 parts of thiophene in 40 parts of ethanol were added 15 parts of ethyl 4-oxo-1-piperidinecarboxylate, 25 parts of 1-(4-fluorophenylmethyl)-N-(4-piperidinyl)-1H-benzimidazol-2-amine and 200 parts of methanol. The whole was hydrogenated at normal pressure and at room temperature with 5 parts of platinum-on-charcoal catalyst 5%. After the calculated amount of hydrogen was taken up, the catalyst was filtered off and the filtrate was evaporated. The residue was purified by column chromatography over silica gel using a mixture of trichloromethane and methanol (90:10 by volume) as eluent. The pure fractions were collected and the eluent was evaporated. The residue was converted into the hydrochloride salt in 2-propanol and 2-propanone. The salt was filtered off and dried, yielding 13.6 parts of ethyl 4-[1-(4-fluorophenylmethyl)-1H-benzimidazol-2ylamino][1,4'-bipiperidine]-1'-carboxylate dihydrochloride monohydrate; mp. 260° C. (171).

In a similar manner there was also prepared:
1-[(4-fluorophenyl)methyl]-N-[1'-(phenylmethyl)-[1,3'-bipiperidin]-4-yl]-1H-benzimidazol-2-amine; mp. 174.6° C. (172).

EXAMPLE 20

To a stirred and cooled (−10° C.) mixture of 12.6 parts of carbon disufide, 5.2 parts of N,N'-methanetetraylbis[cyclohexanamine] and 45 parts of tetrahydrofuran was added dropwise a solution of 8.5 parts of N-[1-(2-aminoethyl)-4-piperidinyl]-1-(2-furanylmethyl)-1H-benzimidazol-2-amine in 45 parts of tetrahydrofuran. Upon completion, stirring was continued overnight at room temperature. The reaction mixture was evaporated and the residue was purified by column chromatography over silica gel using trichloromethane as eluent. The pure fractions were collected and the eluent was evaporated. The residue was crystallized from acetonitrile, yielding 6.7 parts of 1-(2-furanylmethyl)-N-[1-(2-isothiocyanatoethyl)-4-piperidinyl]-1H-benzimidazol-2-amine (173).

EXAMPLE 21

A mixture of 9.4 parts of 1-[(4-fluorophenyl)methyl]-N-[1-[2-[methyl(phenylmethyl)amino]ethyl]-4-piperidinyl]-1H-benzimidazol-2-amine and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was converted into the hydrochloride salt in 2-propanol. The salt was filtered off and dried, yielding 6.3 parts (64%) of 1-[(4-fluorophenyl)methyl]-N-[1-[2-(methylamino)ethyl]-4-piperidinyl]-1H-benzimidazol-2-amine trihydrochloride monohydrate; mp. 232.4° C. (174).

In a similar manner there were also prepared:
1-[(4-fluorophenyl)methyl]-N-[1-[2-[methyl(phenylmethyl)amino]ethyl]-4-piperidinyl]-1H-benzimidazol-2-amine (175); and N-([1,3'-bipiperidin]-4yl)-1-[(4-fluorophenyl)methyl]-1H-benzimidazol-2-amine (176).

EXAMPLE 22

A mixture of 5.7 parts of 1-[4-[[1-[(4-fluorophenyl)methyl]-1H-benzimidazol-2-yl]amino]-1-piperidinyl]-2-propanone, 2.1 parts of hydroxylamine hydrochloride, 20 parts of pyridine, 10 parts of ethanol and 12.5 parts of water was stirred for 3 hours at 65° C. The reaction mixture was poured into water and the whole was alkalized with sodium hydroxide. The product was filtered off and dried, yielding 5.5 parts (93%) of 1-[4-[[1-[(4-fluorophenyl)methyl]-1H-benzimidazol-2-yl]amino]-1-piperidinyl]-2-propanone, oxime; mp. 202° C. (177).

A mixture of 4 parts of 1-[4-[[1-[(4-fluorophenyl)methyl]-1H-benzimidazol-2-yl]amino]-1-piperidinyl]-2-propanone, oxime and 120 parts of methanol saturated with ammonia was hydrogenated at normal pressure and at room temperature with 2 parts of Raney-nickel catalyst. After the calculated amount of hydrogen was taken up, the catalyst was filtered off and the filtrate was evaporated. The residue was crystallized from acetonitrile, yielding 1.3 parts (34%) of N-[1-(2-aminopropyl)-4-piperidinyl]-1-[(4-fluorophenyl)methyl]-1H-benzimidazol-2-amine; mp. 178.3° C. (178).

EXAMPLE 23

A mixture of 2.1 parts of 3-buten-2-one, 9.7 parts of 1-[(4-fluorophenyl)methyl]-N-(4-piperidinyl)-1H-benzimidazol-2-amine and 120 parts of ethanol was stirred for 3 hours at reflux temperature. The reaction mixture was evaporated. The residue was purified by column chromatography over silica gel using a mixture of trichloromethane and methanol (95:5 by volume) as eluent. The pure fractions were collected and the eluent was evaporated. The residue was crystallized from a mixture of 2-propanone and 2,2'-oxybispropane, yielding 5 parts (42%) of 4-[4-[[1-[(4-fluorophenyl)methyl]-1H-benzimidazol-2-yl]amino]-1-piperidinyl]-2-butanone; mp. 131.3° C. (179).

In a similar manner there was also prepared:
1-[4-[[1-[(4-fluorophenyl)methyl]-1H-benzimidazol-2-yl]amino]-1piperidinyl]-3-pentanone dihydrobromide; mp. 202.8° C. (180).

EXAMPLE 24

During 1 hour, gaseous oxirane was bubbled through a stirred mixture of 6 parts of 1-(furanylmethyl)-N-(4-piperidinyl)-1H-benzimidazol-2-amine and 40 parts of methanol. Stirring was continued for 3 hours at room temperature. The reaction mixture was evaporated and the oily residue was converted into the (E)-2-butenedioate salt in ethanol and 2-propanone. The salt was filtered off and dried, yielding 6.5 parts of 4-[[1-(2-furanyl-methyl)-1H-benzimidazol-2-yl]amino]-1-piperidineethanol (E)-2-butenedioate (2:3) monohydrate; mp. 183.2° C. (181)

In a similar manner there was also prepared:
4-[[1-[(4-fluorophenyl)methyl]-1H-benzimidazol-2-yl]amino]-1-piperidineethanol; mp. 138.7° C. (182).

EXAMPLE 25

To a stirred mixture of 37.5 parts of 1-[4-[[1-[(4-fluorophenyl)methyl]-1H-benzimidazol-2-yl]amino]-1-piperidinyl]-3-pentanone dihydrobromide and 500 parts of acetic acid was added a hydrobromic acid solution in glacial acetic acid. Then there were added slowly dropwise 10.5 parts of bromine. Upon completion, stirring was continued overnight at room temperature. The reaction mixture was evaporated and the residue was suspended in 2-propanone. The product was filtered off and dried, yielding 37.5 parts (89%) of 4-bromo-1-[4-[[1-[(4-fluorophenyl)methyl]-1H-benzimidazol-2-yl]amino]-1-piperidinyl]-3-pentanone dihydrobromide (183).

In a similar manner there was also prepared:
1-bromo-4-[4-[[1-[(4-fluorophenyl)methyl]-1H-benzimidazol-2-yl]-amino]-1-piperidinyl]-2-butanone dihydrobromide (184).

EXAMPLE 26

During 2 hours, gaseous ammonia was bubbled through a stirred mixture of 6.7 parts of 1-(2-furanylmethyl)-N-[1-(2-isothiocyanatoethyl)-4-piperidinyl]-1H-benzimidazol-2-amine and 45 parts of tetrahydrofuran. Stirring was continued for 1 hour at room temperature. The reaction mixture was evaporated and the oil residue was crystallized from acetonitrile, yielding 6.2 parts of N-[2-[4-[[1-(2-furanylmethyl)-1H-benzimidazol-2-yl]amino]-1-piperidinyl]ethyl]thiourea; mp. 194.3° C. (185).

Following the same procedure and using equivalent amounts of the appropriate starting materials, there was also prepared:
N-[2-[4-[[1-[(4-fluorophenyl)methyl]-1H-benzimidazol-2-yl]amino]-1-piperidinyl]ethyl]thiourea; mp. 186.1° C. (186).

EXAMPLE 27

To a stirred mixture of 5.3 parts of cyanogen bromide, 106. parts of anhydrous sodium carbonate and 45 parts of tetrahydrofuran was added dropwise a solution of 18.35 parts of N-[1-(2-aminoethyl)-4-piperidinyl]-1-[(4-fluorophenyl)methyl]-1H-benzimidazol-2-amine in tetrahydrofuran at a temperature between −10° C. and −20° C. Upon completion, stirring was continued for 2 hours at −10° C. After heating to 0° C., the whole was filtered and the filtrate was evaporated, yielding 19 parts (100%) of [2[4-[[1-[(4-fluorophenyl)methyl]-1H-benzimidazol-2-yl]amino]-1-piperidinyl]ethyl]cyanimide as a residue (187).

EXAMPLE 28

A mixture of 4.8 parts of 1-isothiocyanato-2,2-dimethoxyethane, 4.2 parts of 4-fluorobenzenemethanamine and 90 parts of tetrahydrofuran was stirred overnight. The reaction mixture was evaporated, yielding 8.9 parts (99%) of N-(2,2-dimethoxyethyl)-N'-[(4-fluorophenyl)methyl]thiourea (188).

In a similar manner there were also prepared:
N-(2,2-dimethoxyethyl)-N'-methylthiourea (189); and
N-(2,2-dimethoxyethyl)-N'-(1-methylethyl)thiourea (109).

EXAMPLE 29

A mixture of 7.1 parts of N-(2,2-dimethoxyethyl)-N'-methylthiourea, 8.5 parts of iodomethane and 80 parts of 2-propanone was stirred overnight. The reaction mixture was evaporated, yielding 12.8 parts (99%) of methyl N-(2,2-dimethoxyethyl)-N'-methylcarbamimidothioate monohydroiodide (191).

In a similar manner there were also prepared:
methyl N-(2,2-dimethoxyethyl)carbamimidothioate monohydroiodide (192);
S-methyl N-(2,2-dimethoxyethyl)-N'-(1-methylethyl)-carbamimidothioate monohydroiodide (193); and
S-methyl N-(2,2-dimethoxyethyl)-N'-[(4-fluorophenyl)methyl]carbamimidothioate monohydroiodide (194).

EXAMPLE 30

A mixture of 12.8 parts of methyl N-(2,2-dimethoxyethyl)-N'-methylcarbamimidothioate monohydroiodide, 13.2 parts of N-[1-(2-aminoethyl)-4-piperidinyl]-1-[(4-fluorophenyl)methyl]-1H-benzimidazol-2-amine and 160 parts of 2-propanol was stirred and refluxed overnight. The reaction mixture was evaporated, yielding 23 parts (99%) of N-(2,2-dimethoxyethyl)-N'-[2-[4-[[1-[(4-fluorophenyl)methyl]-1H-benzimidazol-2-yl]amino]-1-piperidinyl]ethyl]-N''-methylguanidine monohydroiodide (195).

Following the same procedure and using equivalent amounts of the appropriate starting materials, there were also prepared:
N-(2,2-dimethoxyethyl)-N'-[2-[4-[[1-[(4-fluorophenyl)methyl]-1H-benzimidazol-2-yl]amino]-1-piperidinyl]ethyl]guanidine monohydroiodide (196);
N-(2,2-dimethoxyethyl)-N'-[2-[4-[[1-[(4-fluorophenyl)methyl]-1H-benzimidazol-2-yl]amino]-1-piperidinyl]ethyl]-N''-(1-methylethyl)guanidine monohydroiodide (197); and
N-(2,2-dimethoxyethyl)-N''-[(4-fluorophenyl)methyl]-N'-[2-[4-[[1-[(4-fluorophenyl)methyl]-1H-benzimidazol-2-yl]amino]-1-piperidinyl]ethyl]guanidine monohydroiodide (198).

EXAMPLE 31

A mixture of 20 parts of N-[(3,4-dichlorophenyl)methyl]-1,2-benzenediamine, 33 parts of 1-[(4-fluorophenyl)methyl]-N-[1-(2-isothiocyanatoethyl)-4-piperidinyl]-1H-benzimidazol-2-amine and 450 parts of tetrahydrofuran was stirred and refluxed overnight. The reaction mixture was evaporated. The residue was purified by column chromatography over silica gel using a mixture of trichloromethane and methanol (95:5 by volume) as eluent. The pure fractions were collected and the eluent was evaporated, yielding 40 parts (78.9%) of N-[2-[[(3,4-dichlorophenyl)methyl]amino]-phenyl]-N'-[2-[4-[[1-[(4-fluorophenyl)methyl]-1H-benzimidazol-2-yl]amino]-1-piperidinyl]ethyl]thiourea (199).

EXAMPLE 32

A mixture of 57 parts of 1-ethyl-1,4-dihydro-5H-tetrazol-5one, 69 parts of 1,2-dibromoethane, 564 parts of silver carbonate and 900 parts of benzene was stirred and refluxed over weekend using a water separator (in the darkness). The whole was filtered off over Hyflo while hot, washed with trichloromethane and the filtrate was evaporated to dry. The residue was purified by column chromatography over silica gel using trichloromethane as eluent. The second fraction was collected and the eluent was evaporated, yielding 22.3 parts (40%) of 5-(2-bromoethoxy)-1-ethyl-1H-tetrazole (200).

B. Preparation of Final Compounds.

EXAMPLE 33

A mixture of 3.4 parts of 5-(chloromethyl)-4-methyl-1H-imidazole monohydrochloride, 6 parts of 1-(2-furanylmethyl)-N-(4-piperidinyl)-1H-benzimidazol-2-amine, 4.25 parts of sodium carbonate and 135 parts of N,N-dimethylformamide was stirred and heated for 3 hours at 70° C. The reaction mixture was poured onto water and the product was extracted with trichloromethane. The extract was dried, filtered and evaporated. The residue was crystallized from a mixture of acetonitrile and methanol, yielding 4.7 parts (60.2%) of 1-(2-furanylmethyl)-N-[1-[(4-methyl-1H-imidazol-5-yl)methyl]-4-piperidinyl]-1H-benzimidazol-2-amine; mp. 242.1° C. (compound 1).

In a similar manner there were also prepared:

N-[1-(1H-benzimidazol-2-ylmethyl)-4-piperidinyl]-1-(4fluorophenylmethyl)-1H-benzimidazol-2-amine monohydrate; mp. 144.7° C. (compound 2);

1-(4-fluorophenylmethyl)-N-[1-[1-(4-fluorophenylmethyl)-1H-benzimidazol-2-ylmethyl]-4-piperidinyl]-1H-benzimidazol-2-amine; mp. 183.4° C. (compound 3);

1-[(4-fluorophenyl)methyl]-N-[1'-(1-methyl-4-nitro-1H-imidazol-5-yl)[1,4'-bipiperidin]-4-yl]-1H-benzimidazol-2-amine hemihydrate; mp. 147.7° C. (compound 4);

1-[(4-fluorophenyl)methyl]-N-[1'-(1-methyl-4-nitro-1H-imidazol-5-yl)-[1,3'-bipiperidin]-4-yl]-1H-benzimidazol-2-amine; mp. 159.3° C. (compound 5);

1-[(4-fluorophenyl)methyl]-N-[1-[2-[(1-phenyl-1H-tetrazol-5-yl)amino]ethyl]-4-piperidinyl]-1H-benzimidazol-2-amine; mp. 171.3° C. (compound 6);

1-(4-fluorophenylmethyl)-N-[1-[(4-methyl-1H-imidazol-5-yl)methyl]-4-piperidinyl]-1H-benzimidazol-2-amine; mp. 228.3° C. (compound 7);

1-[(4-fluorophenyl)methyl]-N-[1-[2-(4-methyl-5-thiazolyl)ethyl]-4-piperidinyl]-1H-benzimidazol-2-amine; mp. 153.5° C. (compound 8);

1-(2-furanylmethyl)-N-[1-(2-(4-methyl-5-thiazolyl)ethyl]-4-piperidinyl]-1H-benzimidazol-2-amine; mp. 172.1° C. (compound 9); and N-[1-[2-[(1-ethyl-1H-tetrazol-5-yl)oxy]ethyl]-4-piperidinyl]-1-[(4-fluorophenyl)methyl]-1H-benzimidazol-2-amine (E)-2-butenedioate (2:5); mp. 193.4° C. (compound 10).

EXAMPLE 34

A mixture of 1.62 parts of 5-chloro-1-methyl-4-nitro-1H-imidazole, 3.67 parts of N-[1-(2-aminoethyl)-4-piperidinyl]-3-[(4-fluorophenyl)methyl]-3H-imidazo[4,5-b]pyridin-2-amine, 1.1 parts of sodium carbonate, 0.1 parts of potassium iodide and 90 parts of N,N-dimethylformamide was stirred and heated overnight at 70° C. The reaction mixture was cooled and poured onto water. The product was extracted with 4-methyl-2-pentanone. The extract was dried, filtered and evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from acetonitrile, yielding 2.2 parts (45%) of 3-[(4-fluorophenyl)methyl]-N-[1-[2-[(1-methyl-4-nitro-1H-imidazol-5-yl)amino]ethyl]-4-piperidinyl]-3H-imidazo[4,5-b]pyridin-2-amine; mp. 198.7° C. (compound 11).

Following the same procedure and using the equivalent amounts of the appropriate starting materials, there were also prepared:

1-[(4-fluorophenyl)methyl]-N-[1-[2-(1-methyl-4-nitro-1H-imidazol-5-yl)amino]ethyl]-4-piperidinyl]-1H-benzimidazol-2-amine; mp. 200.8° C. (compound 12);

3-[(4-fluorophenyl)methyl]-N-[1-[3-[(2-thiazolyl)amino]propyl]-4-piperidinyl]-3H-imidazo[4,5-b]pyridin-2-amine; mp. 169.3° C. (compound 13); and 1-[(3,4-dimethylphenyl)methyl]-N-[[1-[2-(2-thiazolyl)amino]ethyl]-4-piperidinyl]-1H-benzimidazol-2-amine trihydrochloride; mp. 229.4° C. (compound 14).

EXAMPLE 35

A mixture of 2.41 parts of 2-bromo-5-methyl-1,3,4-thiadiazole, 5.5 parts of N-[1-(2-aminoethyl)-4-piperidinyl]-1-[(4-fluorophenyl)methyl]-1H-benzimidazol-2-amine, 1.6 parts of sodium carbonate and 45 parts of N,N-dimethylacetamide was stirred and heated overnight at 120° C. The reaction mixture was cooled and poured onto water. The product was extracted with 4-methyl-2-pentanone. The extract was dried, filtered and evaporated. The residue was purified by column chromatography over silica gel using a mixture of trichloromethane and methanol saturated with ammonia, (96:4 by volume) as eluent. The pure fractions were collected and the eluent was evaporated. The residue was crystallized from acetonitrile, yielding 2.5 parts (35.8%) of 1-[(4-fluorophenyl)methyl]-N-[1-[2-[(5-methyl-1,3,4-thiadiazol-2-yl)amino]ethyl]-4-piperidinyl]-1H-benzimidazol-2-amine; mp. 190.6° C. (compound 15).

In a similar manner there were also prepared:

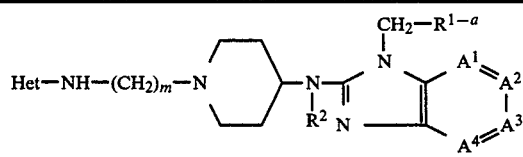

| No. | Het | m | $R^{1-a}$ | $R^2$ | $A^1=A^2-A^3=A^4$ | base or salt | mp. in °C. |
|---|---|---|---|---|---|---|---|
| 16 | 2-thiazolyl | 2 | 4-fluorophenyl | H | CH=CH—CH=CH | base | 175.5 |
| 17 | 2-thiazolyl | 2 | 4-fluorophenyl | H | N=CH—CH=CH | base | 182.4 |

-continued

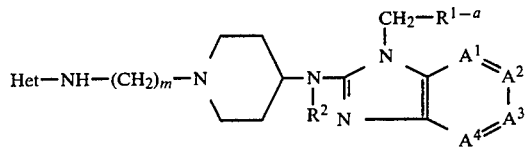

| No. | Het | m | $R^{1-a}$ | $R^2$ | $A^1=A^2-A^3=A^4$ | base or salt | mp. in °C. |
|---|---|---|---|---|---|---|---|
| 18 | 5-amino-1,3,4-thiadiazol-2-yl | 2 | 4-fluorophenyl | H | CH=CH—CH=CH | base | 183.8 |
| 19 | 2-benzothiazolyl | 2 | 4-fluorophenyl | H | CH=CH—CH=CH | base | 198.2 |
| 20 | 2-thiazolyl | 3 | 4-fluorophenyl | H | CH=CH—CH=CH | base | 157.0 |
| 21 | 2-thiazolyl | 5 | 4-fluorophenyl | H | CH=CH—CH=CH | base | 143.4 |
| 22 | 2-thiazolyl | 2 | 4-fluorophenyl | H | CH=CH—N=CH | base | 193.1 |
| 23 | 2-thiazolyl | 2 | 4-fluorophenyl | H | CH=N—CH=CH | 3(COOH)$_2$ H$_2$O | 163.0 |
| 24 | 2-thiazolyl | 2 | 4-methoxyphenyl | H | CH=CH—CH=CH | base | 168.4 |
| 25 | 2-thiazolyl | 2 | 4-chlorophenyl | H | CH=CH—CH=CH | base | 159.1 |
| 26 | 2-thiazolyl | 2 | 4-fluorophenyl | CH$_3$ | CH=CH—CH=CH | 3HCl H$_2$O | 219.3 |
| 27 | 2-thiazolyl | 2 | 2-pyridinyl | H | CH=CH—CH=CH | * | 192.6 |
| 28 | 2-thiazolyl | 2 | 2-thienyl | H | CH=CH—CH=CH | 2(COOH)$_2$ | 211.4 |
| 29 | 2-thiazolyl | 2 | 2-methylphenyl | H | CH=CH—CH=CH | * | 170.1 |
| 30 | 2-thiazolyl | 2 | 3-methylphenyl | H | CH=CH—CH=CH | 2(COOH)$_2$ | 226.5 |
| 31 | 2-thiazolyl | 2 | 2-fluorophenyl | H | CH=CH—CH=CH | base | 112.1 |
| 32 | 5-nitro-2-thiazolyl | 2 | 4-fluorophenyl | H | CH=CH—CH=CH | * | 215.2 |
| 33 | 5-ethyl-1,3,4-thiadiazol-2-yl | 2 | 4-fluorophenyl | H | CH=CH—CH=CH | base | 181.6 |
| 34 | 2-thiazolyl | 2 | H | H | CH=CH—CH=CH | * | 202.5 |
| 35 | 2-thiazolyl | 2 | 4-aminophenyl | H | CH=CH—CH=CH | base | 186.6 |
| 36 | 2-thiazolyl | 2 | 2-Br, 4-F—phenyl | H | CH=CH—CH=CH | **.H$_2$O | 178.5 |
| 37 | 2-thiazolyl | 2 | 4-fluorophenyl | H | CH=CH—CH=CH 5(and 6)F | base | 188.0 |
| 38 | 2-thiazolyl | 2 | 3-fluorophenyl | H | CH=CH—CH=CH | base | 115.1 |
| 39 | 2-thiazolyl | 2 | 4-fluorophenyl | H | CH=CH—CH=CH 5-methyl | base | 192.8 |
| 40 | 2-thiazolyl | 2 | 4-fluorophenyl | H | CH=CH—CH=CH 6-methoxy | base | 207.8 |
| 41 | 2-thiazolyl | 2 | 4-fluorophenyl | H | CH=CH—CH=CH 5-methoxy | base | 143.3 |
| 42 | 4-thiazolyl-methyl | 2 | 4-fluorophenyl | H | CH=CH—CH=CH | ** | 181.7 |
| 43 | 2-thiazolyl | 2 | 4-nitrophenyl | H | CH=CH—CH=CH | *** | 192.8 |
| 44 | 2-thiazolyl | 2 | 2,6-F$_2$—phenyl | H | CH=CH—CH=CH | * H$_2$O | 174.0 |

*(E)—2-butenedioate (1:2)
**(E)—2-butenedioate (1:3)
***cyclohexanesulfamate (1:2)

In a similar manner there were also prepared:
1-phenyl-N-[1-[2-(2-thiazolylamino)ethyl]-4-piperidinyl]-1H-benzimidazol-2-amine trihydrochloride.monohydrate; mp. 240.5° C. (compound 45); N-[1-[2-(2-triazolylamino)ethyl]-4-piperidinyl]-1H-benzimidazol-2-amine; mp. 243.3° C. (compound 46); and cis-N-[1-[2-(2-thiazolylamino)ethyl)-3-methyl-4-piperidinyl]-1-(2-thienylmethyl)-1H-benzimidazolyl-2-amine; mp. 105.8° C. (compound 47).

EXAMPLE 36

A mixture of 2.7 parts of 2-bromothiazole, 5.1 parts of N-[1-(2-aminoethyl)-4-piperidinyl]-1-(2-furanylmethyl)-1H-benzimidazol-2-amine, 5 parts of sodium carbonate, 0.1 parts of sodium iodide and 9 parts of N,N-dimethylacetamide was stirred for 3 hours at about 140° C. Water was added and the product was extracted with 4-methyl-2-pentanone. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from acetonitrile, yielding 3 parts of 1-(2-furanylmethyl)-N-[1-[2-(2-thiazolylamino)ethyl]-4-piperidinyl]-1H-benzimidazol-2-amine; mp. 153.1° C. (compound 48).

In a similar manner there was also prepared:
N-[1-[2-(2-thiazolylamino)ethyl]-4-piperidinyl]-1-(4-thiazolylmethyl)-1H-benzimidazol-2-amine ethanedioate (2:5); mp. 201.8° C. (compound 49).

EXAMPLE 37

A mixture of 2.5 parts of 2-bromothiazole, 5.72 parts of 1-[(4-fluorophenyl)methyl]-N-[1-[2-(methylamino)ethyl]-4-piperidinyl]-1H-benzimidazol-2-amine, 1.6 parts of sodium carbonate, 0.1 parts of potassium iodide and 27 parts of N,N-dimethylacetamide was stirred and heated overnight at 140° C. The reaction mixture was poured onto water. The product was extracted with 4-methyl-2-pentanone. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from 1,1'-oxybisethane, yielding 3.5 parts (50%) of 1-[(4-fluorophenyl)methyl]-N-[1-[2-[methyl(2-thiazolyl- )amino]ethyl]-4-piperidinyl]-1H-benzimidazol-2-amine; mp. 143.2° C. (compound 50).

Following the same procedure and using the equivalent amounts of the appropriate starting materials, there were also prepared:

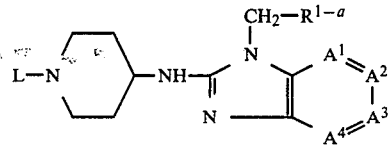

| No. | L | $R^{1-a}$ | $A^1=A^2-A^3=A^4$ | base or salt | mp. in °C. |
|---|---|---|---|---|---|
| 51 | 2-[(5-amino-1,3,4-thiadiazol-2-yl)amino]ethyl | 2-pyridinyl | N=CH—CH=CH | base | 150.0 |
| 52 | 1-(2-thiazolyl)-4-piperidinyl | 4-fluorophenyl | CH=CH—CH=CH | base | 199.9 |
| 53 | 4-(2-thiazolylamino)butyl | 4-fluorophenyl | CH=CH—CH=CH | base | 166.1–167.8 |
| 54 | 2-[(phenylmethyl)(2-thiazolyl)amino]ethyl | 4-fluorophenyl | CH=CH—CH=CH | * | 211.5–212.7 |
| 55 | 2-(2-thiazolylamino)propyl | 4-fluorophenyl | CH=CH—CH=CH | * | 164.5–170.0 |
| 56 | 2-(2-thiazolylamino)ethyl | 2-furanyl | N=CH—CH=CH | * | 176.1–178.9 |
| 57 | 2-(2-thiazolylamino)ethyl | 2-pyridinyl | N=CH—CH=CH | ** | 194.2 |
| 58 | 2-(2-thiazolylamino)ethyl | 4-fluorophenyl | CH=CH—CH=CH | *** | 150.1 |
| 59 | 2-(2-thiazolylamino)ethyl | 3-pyridinyl | CH=CH—CH=CH | base | 130.9 |
| 60 | 2-(2-thiazolylamino)ethyl | 2-thienyl | N=CH—CH=CH | ** | 202.4 |
| 61 | 2-(2-thiazolylamino)ethyl | phenyl | CH=CH—CH=CH | base | 123.7 |
| 62 | 2-(2-thiazolylamino)ethyl | 4-methylphenyl | CH=CH—CH=CH | * | 166.7 |
| 63 | 2-(2-thiazolylamino)ethyl | 3-chlorophenyl | CH=CH—CH=CH | base | 118.3 |
| 64 | 2-(2-thiazolylamino)ethyl | 2-iodophenyl | CH=CH—CH=CH | * | 164.6 |

*(E)—2-butenedioate (1:2)
**(E)—2-butenedioate (1:3)
***ethanedioate (1:3)

EXAMPLE 38

A mixture of 4 parts of 2-chloro-1-[(4-fluorophenyl)methyl]-1H-benzimidazole, 6.1 parts of N-[1-[(4-fluorophenyl)methyl]-1H-benzimidazol-2-yl]-[1,4'-bipiperidine]-4-amine and 1 part of potassium iodide was stirred and heated for 3 hours at 130° C. The reaction mixture was cooled and taken up in water and trichloromethane. The whole was alkalized with potassium carbonate. The organic phase was separated, dried, filtered and evaporated. The residue was purified by HPLC using a mixture of trichloromethane and methanol (98:2 by volume), saturated with ammonia, as eluent. The pure fractions were collected and the eluent was evaporated. The residue was crystallized from acetonitrile, yielding 1.6 parts of 1-[(4-fluorophenyl)methyl]-N-[1'-[1-[(4-fluorophenyl)methyl]-1H-benzimidazol-2-yl]-[1,4'-bipiperidin]-4-yl]-1H-benzimidazol-2-amine monohydrate; mp. 130.2° C. (compound 65).

EXAMPLE 39

A mixture of 5.25 parts N-(1H-benzimidazol-2-yl)guanidine and 11.01 parts of N-[1-(2-aminoethyl)-4-piperidinyl]-1-[(4-fluorophenyl)methyl]-1H-benzimidazol-2-amine was stirred and heated for 20 hours at 180° C. After cooling, the residue was purified by column chromatography (HPLC) over silica gel using a mixture of trichloromethane and methanol, saturated with ammonia, (85:15 by volume) as eluent. The pure fractions were collected and the eluent was evaporated. The residue was crystallized from 2-propanone and 2,2'-oxybispropane. The product was filtered off and dried, yielding 1.8 parts (9%) of N-(1H-benzimidazol-2-yl)-N'-[2-[4-[[1-[(4-fluorophenyl)methyl]-1H-benzimidazol-2-yl]amino]-1-piperidinyl]ethyl]guanidine trihydrochloride.dihydrate; mp. 245.9° C. (compound 66).

EXAMPLE 40

To a stirred mixture of 5.5 parts of 4-[1-[(4-fluorophenyl)-methyl]-1H-benzimidazol-2-ylamino]-1-piperidineethanol and 135 parts of N,N-dimethylformamide were added 0.75 parts of a sodium hydride dispersion 50%. After stirring for 30 minutes at room temperature, 2.54 parts of 2-chlorobenzothiazole were added and the whole was further stirred for 3 hours. The reaction mixture was poured onto water and the product was extracted with 4-methyl-2-pentanone. The extract was dried, filtered and evaporated. The residue was purified by column chromatography over silica gel using a mixture of trichloromethane and methanol (96:4 by volume) saturated with ammonia, as eluent. The pure fractions were collected and the eluent was evaporated. The residue was crystallized from acetonitrile, yielding 4.6 parts (61%) of N-[1-[2-(2-benzothiazolyloxy)ethyl]-4-piperidinyl]-1-[(4-fluorophenyl)methyl]-1H-benzimidazol-2-amine; mp. 147.0° C. (compound 67).

In a similar manner there were also prepared:
N-[1-[2-[[1-[(4-fluorophenyl)methyl]-1H-benzimidazol-2-yl]oxy]ethyl]-4-piperidinyl]-1-(2-furanylmethyl)-1H-benzimidazol-2-amine; mp. 182.2° C. (compound 68);
1-[(4-fluorophenyl)methyl]-N-[1-[2-[[1-[(4-fluorophenyl)methyl]-1H-benzimidazol-2-yl]oxy]ethyl]-4-piperidinyl]-1H-benzimidazol-2-amine; mp. 153.8° C. (compound 69); and
N-[1-[2-(2-benzothiazolyloxy)ethyl]-4-piperidinyl]-1-(2-furanylmethyl)-1H-benzimidazol-2-amine (E)-2-butenedioate (1:2); mp. 166.1° C. (compound 70).

EXAMPLE 41

To a stirred mixture of 5.1 parts of 4-[[1-(2-furanylmethyl)-1H-benzimidazol-2-yl]amino]-1-piperidineethanol and 100 parts of dimethyl sulfoxide were added portionwise 0.9 parts of a sodium hydride dispersion 50%.

After stirring for 1 hour at room temperature, 2.5 parts of 2-bromothiazole were added dropwise. Upon completion, stirring was continued overnight at room temperature. Water was added and the product was extracted twice with trichloromethane. The combined extracts were dried, filtered and evaporated. The residue was taken up in 4-methyl-2-pentanone. The organic phase was washed with water, dried, filtered and evaporated. The residue was purified by column chromatography over silica gel using a mixture of trichloromethane and methanol (90:10 by volume) as eluent. The pure fractions were collected and the eluent was evaporated. The residue was crystallized from methylbenzene, yielding 0.3 parts of 1-(2-furanylmethyl)-N-[1-[2-(2-thiazolyloxy)ethyl]-4-piperidinyl]-1H-benzimidazol-2-amine; mp. 136.4° C. (compound 71).

EXAMPLE 42

To a stirred and cooled (below 10° C.) mixture of 5.52 parts of 4-[[1-[(4-fluorophenyl)methyl]-1H-benzimidazol-2-yl]amino]-1-piperidine ethanol, 100 parts of dimethyl sulfoxide and 90 parts of methylbenzene were added 0.75 parts of a sodium hydride dispersion 50%. After stirring for 30 minutes at a temperature below 10° C., 2.5 parts of 2-bromothiazole were added and stirring was continued overnight while the mixture was allowed to reach room temperature. The reaction mixture was poured onto water and the product was extracted with 4-methyl-2-pentanone. The extract was dried, filtered and evaporated. The residue was purified by column chromatography over silica gel using a mixture of trichloromethane and methanol (96:4 by volume) saturated with ammonia, as eluent. The pure fractions were collected and the eluent was evaporated. The residue was crystallized from acetonitrile, yielding 1 part (14.5%) of 1-[(4-fluorophenyl)methyl]-N-[1-[2-(2-thiazolyloxy)ethyl]-4-piperidinyl]-1H-benzimidazol-2-amine; mp. 156.5° C. (compound 72).

EXAMPLE 43

A mixture of 1.5 parts of 2-benzoxazolethiol, 4.6 parts of N-[1-(2-chloroethyl)-4-piperidinyl]-1-[(4-fluorophenyl)methyl]-1H-benzimidazol-2-amine, 4.2 parts of potassium carbonate and 120 parts of 2-propanone was stirred and refluxed overnight. The reaction mixture was evaporated and the residue was taken up in water. The product was extracted with dichloromethane. The extract was dried, filtered and evaporated. The residue was purified by column chromatography over silica gel using a mixture of trichloromethane and methanol (96:4 by volume) as eluent. The pure fractions were collected and the eluent was evaporated. The residue was crystallized from acetonitrile, yielding 2.5 parts (50%) of N-[1-[2-[(2-benzoxazolyl)thio]ethyl]-4-piperidinyl]-1-[(4-fluorophenyl)methyl]-1H-benzimidazol-2-amine; mp. 174.2° C. (compound 73).

In a similar manner there were also prepared:
N-[1-[2-[(1-ethyl-1H-tetrazol-5-yl)thio]ethyl]-4-piperidinyl]-1-[(4-fluorophenyl)methyl]-1H-benzimidazol-2-amine; mp. 155.9° C. (compound 74); and
1-[(4-fluorophenyl)methyl]-N-[1-[2-[(1-methyl-1H-imidazol-2-yl)thio]ethyl]-4-piperidinyl]-1H-benzimidazol-2-amine; mp. 150.2° C. (compound 75).

EXAMPLE 44

A mixture of 1.6 parts of 1H-indole-2-carboxylic acid, 3.67 parts of N-[1-(2-aminoethyl)-4-piperidinyl]-1-[(4-fluorophenyl)methyl]-1H-benzimidazol-2-amine, 2.1 parts of N,N'-methanetetraylbis[cyclohexanamine] and 195 parts of dichloromethane was stirred over weekend at room temperature. The reaction mixture was filtered over Hyflo and the filtrate was evaporated. The residue was purified by column chromatography over silica gel using a mixture of trichloromethane and methanol (95:5 by volume) as eluent. The pure fractions were collected and the eluent was evaporated. The residue was crystallized from acetonitrile, yielding 1 parts (19.5%) of N-[2-[4-[[1-[(4-fluorophenyl)methyl]-1H-benzimidazol-2-yl]amino]-1-piperidinyl]ethyl]-1H-indole-2-carboxamide; mp. 232.1° C. (compound 76).

EXAMPLE 45

To a stirred mixture of 3.5 parts of 1H-indol-3-acetic acid, 4.05 parts of N,N-diethylethanamine and 260 parts of dichloromethane were added 5.1 parts of 2-chloro-1-methylpyridinium iodide and stirring was continued for 15 minutes at room temperature. Then there were added 7.2 parts of N-[1-(2-aminoethyl)-4-piperidinyl]-1-[(4-fluorophenyl)methyl]-1H-benzimidazol-2-amine and the whole was stirred for 1 hour at room temperature. The reaction mixture was poured onto water and the layers were separated. The organic phase was dried, filtered and evaporated. The residue was purified by column chromatography over silica gel using a mixture of trichloromethane and methanol (96:4 by volume) saturated with ammonia, as eluent. The pure fractions were collected and the eluent was evaporated. The residue was crystallized from acetonitrile, yielding 4.5 parts (43%) of N-[2-[4-[[1-[(4-fluorophenyl)methyl]-1H-benzimidazol-2-yl]amino]-1-piperidinyl]ethyl]-1H-indol-3-acetamide; mp. 193.6° C. (compound 77).

In a similar manner there was also prepared:
N-[2-[4-[[1-[(4-fluorophenyl)methyl]-1H-benzimidazol-2-yl]amino]-1piperidinyl]ethyl]-1-methyl-1H-indole-2-carboxamide; mp. 140.3° C. (compound 78).

EXAMPLE 46

A mixture of 12.5 parts of N-(2,2-dimethoxyethyl)-N'-[2-[4-[[1-[(4-fluorophenyl)methyl]-1H-benzimidazol-2-yl]amino]-1-piperidinyl]ethyl]guanidine monohydroiodide and 100 parts of a hydrochloric acid solution 10% was stirred and refluxed for 1 hour. The reaction mixture was poured onto crushed ice. The whole was treated with a sodium hydroxide solution. The product was extracted with dichloromethane. The extract was dried, filtered and evaporated. The solid residue was crystallized from 4-methyl-2-pentanone. The product was filtered off and dried, yielding 2.3 parts (26%) of 1-[(4-fluorophenyl)methyl]-N-[1-[2-(1H-imidazol-2-ylamino)ethyl]-4-piperidinyl]-1H-benzimidazol-2-amine; mp. 226.5° C. (compound 79).

In a similar manner there were also prepared:
1-[(4-fluorophenyl)methyl]-N-[1-[2-[(1-methyl-1H-imidazol-2-yl)amino]ethyl]-4-piperidinyl]1H-benzimidazol-2-amine hemihydrate; mp. 85.0° C. (compound 80);
1-[(4-fluorophenyl)methyl]-N-[1-[2-[[1-(1-methylethyl)-1H-imidazol-2-yl]amino]-ethyl]-4-piperidinyl]-1H-benzimidazol-2-amine mono hydrate; mp. 90.8° (compound 81); and
1-[(4-fluorophenyl)methyl]-N-[1-[2-[[1-[(4-fluorophenyl)methyl]-1H-imidazol-2-yl]amino]ethyl]-4-piperidinyl]-1H-benzimidazol-2-amine cyclohexanesulfamate(1:3).dihydrate; mp. 230°-250° C. (dec) (compound 82).

EXAMPLE 47

A mixture of 40 parts of N-[2-[[(3,4-dichlorophenyl)methyl]amino]phenyl]-N'-[2-[4-[[1-[(4-fluorophenyl)methyl]-1H-benzimidazol-2-yl]amino]-1-piperidinyl]ethyl]thiourea, 60 parts of mercury(II)oxide, 0.1 parts of sulfur and 400 parts of ethanol was stirred and refluxed overnight. The reaction mixture was filtered over Hyflo and the filtrate was evaporated. The residue was crystallized from ethanol. The product was filtered off and dried, yielding 17 parts (45%) of 1-[(3,4-dichlorophenyl)methyl]-N-[2-[4-[[1-[(4-fluorophenyl)methyl]-1H-benzimidazol-2-yl]amino]1-piperidinyl]ethyl]-1H-benzimidazol-2-amine; mp. 113.2° C. (compound 83).

EXAMPLE 48

To a stirred mixture of 1.95 parts of [2-[4-[[1-[(4-fluorophenyl)methyl]-1H-benzimidazol-2-yl]amino]-1-piperidinyl]ethyl]-cyanamide, 45 parts of tetrahydrofuran and 50 parts of water was added a solution of 3.7 parts of 1-hydroxy-2-propanone in water (=50%). 5 Parts of a sodium hydroxide solution 2N were added dropwise. Upon completion, stirring was continued for 2 hours at room temperature. The reaction mixture was poured onto water. The product was extracted with trichloromethane. The extract was dried, filtered and evaporated. The residue was purified by column chromatography over silica gel using a mixture of trichloromethane and methanol, saturated with ammonia, (96:4 by volume) as eluent. The pure fractions were collected and the eluent was evaporated. The residue was crystalized from acetonitrile, yielding 1.3 parts (6%) of 1-[(4-fluorophenyl)methyl]-N-[1-[2-[(4-methyl-2-oxazolyl)amino]ethyl]-4-piperidinyl]-1H-benzimidazol-2-amine; mp. 178.1° C. (compound 84).

EXAMPLE 49

To a stirred mixture of 4.3 parts of N-[2-[4-[[1-[(4-fluorophenyl)methyl]-1H-benzimidazol-2-yl]amino]-1-piperidinyl]ethyl]thiourea, 2.1 parts of potassium carbonate and 45 parts of tetrahydrofuran was added dropwise a solution of 0.9 parts of 1-chloro-2-propanone in a small amount of tetrahydrofuran. Upon completion, stirring at room temperature was continued overnight. The reaction mixture was filtered over Hyflo and the filtrate was evaporated. The residue was crystallized from acetonitrile. The product was filtered off and dried, yielding 3.8 parts (81%) of 1-[(4-fluorophenyl)methyl]-N-[1-[2-[(4-methyl-2-thiazolyl)amino]ethyl]-4-piperidinyl]-1H-benzimidazol-2-amine; mp. 184° C. (compound 85).

In a similar manner there were also prepared:
1-[(4-fluorophenyl)methyl]-N-[1-[2-[[4-(4-pyridinyl-2-thiazolyl)amino]ethyl]-4-piperidinyl]-1H-benzimidazol-2-amine; mp. 195°–212° C. (compound 86); and
1-[(4-fluorophenyl)methyl]-N-[1-[2-[[4-(2-pyridinyl-2-thiazolyl)amino]ethyl]-4-piperidinyl]-1H-benzimidazol-2-amine; mp. 151.5° C. (compound 87).

EXAMPLE 50

A mixture of 1.3 parts of 1-chloro-2-propanone, 5 parts of N-[2-[4-[[1-(2-furanylmethyl)-1H-benzimidazol-2-yl]amino]-1-piperidinyl]ethyl]thiourea, 3 parts of potassium carbonate and 68 parts of N,N-dimethylacetamide was stirred overnight at room temperature. Water was added and the product was extracted with 4-methyl-2-pentanone. The extract was dried, filtered and evaporated. The oily residue was purified by column chromatography over silica gel using a mixture of trichloromethane and methanol (95:5 by volume) as eluent. The pure fractions were collected and the eluent was evaporated. The residue was converted into the hydrochloride salt in 2-propanol. The salt was filtered off and dried overnight in vacuo at 100° C., yielding 3.8 parts of 1-(2-furanylmethyl)-N-[1-[2-[(4-methyl-2-thiazolyl)amino]ethyl]-4-piperidinyl]-1H-benzimidazol-2-amine trihydrochloride monohydrate; mp. 238.5° C. (compound 88).

EXAMPLE 51

To a stirred mixture of 4.3 parts of N-[2-[4-[[1-[(4-fluorophenyl)methyl]-1H-benzimidazol-2-yl]amino]-1-piperidinyl]ethyl]thiourea, 2.1 parts of potassium carbonate and 40 parts of methanol was added dropwise a solution of 2 parts of 2-bromo-1-phenylethanone in methanol. Upon completion, stirring was continued for overnight at room temperature. The reaction mixture was filtered over Hyflo and the filtrate was evaporated. The residue was purified by column chromatography over silica gel using a mixture of trichloromethane and methanol (90:10 by volume) as eluent. The pure fractions were collected and the eluent was evaporated. The residue was crystallized from acetonitrile, yielding 2.5 parts of 1-[(4-fluorophenyl)methyl]-N-[1-[2-[(4-phenyl-2-thiazolyl)amino]ethyl]-4-piperidinyl]-1H-benzimidazol-2-amine; mp. 176.2° C. (compound 89).

EXAMPLE 52

A mixture of 1.2 parts of N-(aminothioxomethyl)-guanidine, 6.3 parts of 1-bromo-4-[4-[[1-[(4-fluorophenyl)methyl]-1H-benzimidazol-2-yl]amino]-1-piperidinyl]-2-butanone dihydrobromide and 120 parts of methanol was stirred overnight at room temperature. The precipitated product was filtered off and dried, yielding 3.6 parts (49%) of N-[4-[2-[4-[[1-[(4-fluorophenyl)methyl]-1H-benzimidazol-2-yl]amino]-1-piperidinyl]ethyl-2-thiazolyl]guanidine trihydrobromide; mp. 282.8° C. (compound 90).

In a similar manner there were also prepared:
N-[1-[2-(2-amino-4-thiazolyl)ethyl]-4-piperidinyl]-1-[(4-fluorophenyl)methyl]-1H-benzimidazol-2-amine; mp. 201.0° C. (compound 91);
1-[(4-fluorophenyl)methyl]-N-[1-[2-(2-phenyl-4-thiazolylethyl]-4-piperidinyl]-1H-benzimidazol-2-amine dihydrochloride monohydrate; mp. 258.1° C. (compound 92);
1-[(4-fluorophenyl)methyl]-N-[1-[2-(2-methyl-4-thiazolylethyl]-4-piperidinyl]-1H-benzimidazol-2-amine monohydrate; mp. 113.3° C. (compound 93);
N-[1-[2-(2-amino-5-methyl-4-thiazolyl)ethyl]-4-piperidinyl]-1-[(4-fluorophenyl)methyl]-1H-benzimidazol-2-amine; mp. 214.4° C. (compound 94);
1-[(4-fluorophenyl)methyl]-N-[1-[2-(5-methyl-2-phenyl-4-thiazolylethyl]-4-piperidinyl]-1H-benzimidazol-2-amine monohydrate; mp. 127.4° C. (compound 95); and
1-[(4-fluorophenyl)methyl]-N-[1-[2-[2-(phenylamino)-4-thiazolyl]-ethyl]-4-piperidinyl]-1H-benzimidazol-2-amine trihydrochloride; mp. 233.4°–237.9° C. (compound 96).

EXAMPLE 53

A mixture of 1.5 parts of isothiocyanatomethane and 150 parts of methanol saturated with ammonia was stirred for 1 hour at room temperature. The whole was evaporated and to the residue were added 9.7 parts of 4-bromo-1-[4-[[1-[(4-fluorophenyl)methyl]-1H-benzimidazol-2-yl]amino]-1-piperidinyl]-3-pentanone and 120 parts of methanol. Stirring was continued overnight at room temperature. The reaction mixture was evaporated and the residue was taken up in water. The whole was alkalized with a sodium hydroxide solution and extracted with dichloromethane. The extract was dried, filtered and evaporated. The residue was crystallized from acetonitrile, yielding 5.2 parts (72.5%) of 1-[(4-fluorophenyl)methyl]-N-[1-[2-[5-methyl-2-(methylamino)-4-thiazolyl]ethyl]-4-piperidinyl]-1H-benzimidazol-2-amine; mp. 181.8° C. (compound 97).

Following the same procedure and using equivalent amounts of the appropriate starting materials, there was also prepared:

1-[(4-fluorophenyl)methyl]-N-[1-[2-[2-(methylamino)-4-thiazolyl]-ethyl]-4-piperidinyl]-1H-benzimidazol-2-amine; mp. 157.9° C. (compound 98).

EXAMPLE 54

A mixture of 1.2 parts of 2-chloroethanamine, 4.1 parts of 1-(4-fluorophenylmethyl)-N-[1-(2-isothiocyanatoethyl)-4-piperidinyl]-1H-benzimidazol-2-amine, 2.2 parts of sodium carbonate and 135 parts of tetrahydrofuran was stirred for 3 hours at room temperature. The mixture was heated to reflux and stirring was continued overnight at reflux temperature. The reaction mixture was filtered and the filtrate was evaporated. The residue was purified by column chromatography over silica gel using a mixture of trichloromethane and methanol, saturated with ammonia (95:5 by volume) as eluent. The pure fractions were collected and the eluent was evaporated. The residue was crystallized twice from acetonitrile, yielding 1 part of N-[1-[2-[4,5-dihydro-2-thiazolyl)amino]ethyl]-4-piperidinyl]-1-[(4-fluorophenyl)methyl]-1H-benzimidazol-2-amine; mp. 147.6° C. (compound 99).

EXAMPLE 55

To a stirred mixture of 6.76 parts of 1-[(4-fluorophenyl)methyl]-N-[1-[2-(2-thiazolylamino)ethyl]-4-piperidinyl]-1H-benzimidazol-2-amine, 1.5 parts of N,N-diethylethanamine and 225 parts of trichloromethane was added dropwise a solution of 2.1 parts of benzoyl chloride in trichloromethane. Upon completion, stirring was continued overnight. The reaction mixture was poured into water. The layers were separated. The organic layer was dried, filtered and evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from 2,2'-oxybispropane and 2-propanone. The product was filtered off and dried, yielding 4 parts (48%) of N-[2-[4-[[1-[(4-fluorophenyl)methyl]-1H-benzimidazol-2-yl]amino]-1-piperidinyl]ethyl]-N-(2-thiazolyl)benzamide; mp. 155.9° C. (compound 100).

In a similar manner there was also prepared:
ethyl[2-[4-[[1-[(4-fluorophenyl)methyl]-1H-benzimidazol-2-yl]amino]-1-piperidinyl]ethyl](2-thiazolyl)carbamate; mp. 164.0° C. (compound 101).

EXAMPLE 56

A mixture of 6.76 parts of 1-[(4-fluorophenyl)methyl]-N-[1-[2-2-thiazolylamino]ethyl]-4-piperidinyl]-1H-benzimidazol-2-amine, 15 parts of acetic acid anhydride and 40 parts of acetic acid was stirred and refluxed overnight. The reaction mixture was evaporated and the residue was taken up in water. The whole was alkalized with ammonium hydroxide and the product was extracted with trichloromethane. The extract was dried, filtered and evaporated. The residue was purified by column chromatography over silica gel using a mixture of trichloromethane and methanol (90:10 by volume) as eluent. The second fraction was collected and the eluent was evaporated. The residue was crystallized from acetonitrile, yielding 4.9 parts (66.3%) of N-[2-[4-[[1-[(4-fluorophenyl)methyl]-1H-benzimidazol-2-yl]amino]-1-piperidinyl]ethyl]-N-(2-thiazolyl)acetamide; mp. 185.5°–193.0° C. (compound 102).

EXAMPLE 57

A mixture of 1.1 parts of isocyanatomethane, 6.76 parts of 1-[(4-fluorophenyl)methyl]-N-[1-[2-[2-thiazolylamino]ethyl]-4-piperidinyl]-1H-benzimidazol-2-amine and 90 parts of tetrahydrofuran was stirred and refluxed overnight. The reaction mixture was evaporated. The residue was crystallized from acetonitrile, yielding 4.5 parts (59%) of N-[2-[4-[[1-[(4-fluorophenyl)methyl]-1H-benzimidazol-2-yl]amino]-1-piperidinyl]ethyl]-N'-methyl-N-(2-thiazolyl)urea; mp. 171.9° C. (compound 103).

EXAMPLE 58

A mixture of 1.1 parts of isothiocyanatomethane, 6.76 parts of 1-[(4-fluorophenyl)methyl]-N-[1-[2-[2-thiazolylamino]ethyl]-4-piperidinyl]-1H-benzimidazol-2-amine and 90 parts of tetrahydrofuran was stirred and refluxed for one week. The reaction mixture was evaporated. The residue was purified by column chromatography over silica gel using a mixture of trichloromethane and methanol (90:10 by volume) as eluent. The pure fractions were collected and the eluent was evaporated. The residue was crystallized from methanol, yielding 3.5 parts (44.5%) of N-[2-[4-[[1-[(4-fluorophenyl)methyl]-1H-benzimidazol-2-yl]amino]-1-piperidinyl]ethyl]-N'-methyl-N-(2-thiazolyl)thiourea; mp. 188.5° C. (compound 104).

EXAMPLE 59

A mixture of 1.7 parts of 2-chloropyrimidine, 4.3 parts of 1-[(4-fluorophenyl)methyl]-N-[1-[2-(1H-imidazol-2-ylamino)ethyl]-4-piperidinyl]-1H-benzimidazol-2-amine, 3.2 parts of sodium carbonate, 0.1 parts of sodium iodide and 67.5 parts of N,N-dimethylacetamide was stirred and heated overnight at 120° C. After cooling, the reaction mixture was poured into water. The product was extracted with 4-methyl-2-pentanone. The extract was dried, filtered and evaporated. The residue was dissolved in 1,1'-oxybisethane. The whole was filtered over activated charcoal and the filtrate was evaporated. The residue was converted into the ethanedioate salt in ethanol and acetonitrile. The salt was filtered off and dried, yielding 2.3 parts (28%) of (1-[(4-fluorophenyl)methyl]-N-[1-[2-[[1-(2-pyrimidinyl)-1H-imidazol-2-yl]amino]ethyl]-4-piperidinyl]-1H-benzimidazol-2amine ethanedioate(1:3); mp. 149.6° C. (compound 105).

In a similar manner there was also prepared:
N-[1-[2-[[1-[1-(4-chlorophenyl)ethyl]-1H-imidazol-2-yl]amino]ethyl]-4-piperidinyl]-1-[(4-fluorophenyl)methyl]-1H-benzimidazol-2-amine cyclohexanesulfamate(1:3).dihydrate; mp. 148.2° C. (compound 106).

EXAMPLE 60

To a stirred mixture of 0.8 parts of lithium aluminum hydride and 135 parts of tetrahydrofuran were added slowly 4 parts of N-[2-[4-[[1-[(4-fluorophenyl)methyl]-1H-benzimidazol-2-yl]amino]-1-piperidinyl]ethyl]-1H-indol-3-acetamide. The whole was stirred and refluxed overnight. The reaction mixture was cooled in an ice bath and decomposed by the successive additions of 1 part of water, 4.5 parts of a sodium hydroxide solution 15% and 3 parts of water. The whole was filtered over Hyflo and the filtrate was evaporated. The residue was purified by column chromatography over silica gel using a mixture of trichloromethane and methanol (96:4 by volume) saturated with ammonia, as eluent. The pure fractions were collected and the eluent was evaporated. The residue was crystallized from acetonitrile, yielding 1 part (25.5%) of 1-[(4-fluorophenyl)methyl]-N-[1-[2-[[2-(1H-indol-3-yl)ethyl]amino]ethyl]-4-piperidinyl]-1H-benzimidazol-2-amine; mp. 169.7° C. (compound 107).

In a similar manner there was also prepared:
1-[(4-fluorophenyl)methyl]-N-[1-[2-(1H-indol-3-yl)ethyl]-4-piperidinyl]-1H-benzimidazol-2-amine; mp. 178.4° C. (compound 108).

EXAMPLE 61

A mixture of 6.4 parts of 1-[(3,4-dichlorophenyl)methyl]-N-[2-[4-[[1-[(4-fluorophenyl)methyl]-1H-benzimidazol-2-yl]amino]-1-piperidinyl]ethyl]-1H-benzimidazol-2-amine, 2 parts of calcium oxide and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. Water was added and the product was extracted with trichloromethane. The extract was dried, filtered and evaporated. The residue was crystallized from acetonitrile. The product was filtered off and dried, yielding 4.8 parts (84%) of N-[2-[[4-[1-[(4-fluorophenyl)methyl]-1H-benzimidazol-2-yl]amino]-1-piperidinyl]ethyl]-1-(phenylmethyl)-1H-benzimidazol-2-amine; mp. 198.4° C. (compound 109).

The useful antihistaminic properties of the compounds of formula (I) are demonstrated in the following test procedure.

Protection of rats from compound 48/80-induced lethality.

Compound 48/80, a mixture of oligomers obtained by condensation of 4-methoxy-N-methylbenzeneethanamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test compounds. Male rats of an inbred Wistar strain, weighing 240–260 g were used in the experiment. After overnight starvation the rats were transferred to conditioned laboratories (temp.=21±1° C., relative humidity=65±5%).

The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration.

The $ED_{50}$-values of the compounds of formula (I) are listed in the first column of table 1. Said $ED_{50}$-values are the values in mg/kg body weight at which the tested compounds protect 50% of the tested animals against compound 48/80-induced lethality.

The compounds of formula (I) and the pharmaceutically acceptable acid addition salts thereof are also potent serotonin-antagonists. The potency of the subject compounds as serotonin-antagonists is clearly evidenced by the results obtained in the following tests wherein the antagonistic activity of the subject compounds on the effect of serotonin is examined.

Antagonistic activity on the effects of serotonin in the gastric lesion test.

A. Lesions induced by compound 48/80:

Compound 48/80 (a mixture of oligomers obtained by condensation of 4-methoxy-N-methylbenzeneethanamine and formaldehyde) is a potent releaser of vasoactive amines from endogenous stores such as, for example, histamine and serotonin. Rats injected with compound 48/80 exhibit consistent changes of blood flow in different vascular beds: cyanosis of the ears and the extremities are prominent within five minutes after injection of the compound; the rats die from shock within 30 minutes. The shock, followed by dead, can be avoided if the rats are pretreated with a classical H 1 antagonist.

However the stimulatory effects on gastric secretion are not suppressed so that rats treated with compound 48/80 and protected from shock by an H 1 antagonist may exhibit all signs of intensive gastric gland activity: gross autopsy shows distended stomachs with abnormal contents and rough bright red patches all over the mucosa, corresponding to areas of disintegrated glands. A number of known serotonin-antagonists such as, for example, methysergide, cyproheptadine; cinanserin, mianserin, pipamperone, spiperone, pizotifen and metergoline, prevent completely the cyanosis of ears and extremities as well as the lesions in the glandular area of the stomach and the abnormal gastric distension.

B. Method:

Male rats of a Wistar inbred strain, weighing 220–250 g, were starved overnight, water being available ad libitum. The test compounds were administered orally as a solution or as a suspension in aqueous medium. A control rat and a "blank" rat received the test compound. One hour later 5-[4-(diphenylmethyl)-1-piperazinylmethyl]-1-methyl-1H-benzimidazole-2-methanol was administered subcutaneously to all rats at the dose of 2.5 mg/kg. Two hours after the oral or subcutaneous administration of the test compound, the compound 48/80 (freshly solved in water at a concentration of 0.25 mg/ml) was injected intravenously into all rats (dose: 1 mg/kg) except the "blank" rats.

Four hours after the intravenous injection of compound 48/80, the rats were decapitated and the stomachs were removed. Subsequently the stomachs were inspected for distension and contents (blood, fluid, food) and thoroughly rinsed. The macroscopic lesions were scored from 0 to +++, 0 corresponding to the complete absence of visible lesions and the highest score corresponding to reddish rough patches covering more than half the glandular area.

The second column of Table 1 shows for a number of compounds of formula (I) the doses (in mg/kg body weight) at which the distension of the stomach as well as the lesions in the glandular area of the stomach are completely absent in 50% of the test rats ($ED_{50}$-value).

The compounds listed in Table 1 are not given for the purpose of limiting the invention thereto but only to exemplify the useful pharmacological activities of all the compounds within the scope of formula (I).

TABLE 1

| Compound No. | Column 1<br>compound 48/80<br>lethality test in<br>rats-$ED_{50}$ in mg/kg<br>body weight | Column 2<br>gastric lesion<br>test<br>$ED_{50}$ in mg/kg<br>body weight |
|---|---|---|
| 2 | 0.63 | — |
| 7 | 0.02 | 0.31 |
| 10 | 0.04 | — |
| 12 | 0.31 | — |
| 15 | 0.04 | 0.31 |
| 16 | 0.08 | — |
| 17 | 0.02 | 0.16 |
| 18 | 0.02 | 0.04 |
| 19 | 0.31 | — |
| 20 | 0.16 | — |
| 21 | 0.16 | 0.31 |
| 23 | 0.08 | — |
| 24 | 0.31 | — |
| 25 | 0.31 | 0.63 |
| 26 | 0.02 | — |
| 27 | 0.04 | — |
| 28 | 0.08 | 0.02 |
| 29 | 0.63 | 0.63 |
| 31 | 0.08 | 0.63 |
| 32 | 0.63 | — |
| 33 | 0.16 | — |
| 35 | 0.31 | — |
| 37 | 0.08 | 0.08 |
| 43 | 0.31 | — |
| 48 | 0.08 | 0.63 |
| 49 | 0.04 | 0.63 |
| 50 | 0.08 | — |
| 52 | 1.25 | 0.63 |
| 53 | 0.31 | — |
| 56 | 0.01 | — |
| 57 | 0.005 | — |
| 58 | 0.02 | 0.04 |
| 62 | 0.16 | 0.63 |
| 66 | 0.31 | — |
| 67 | 0.63 | — |
| 72 | 0.08 | 0.63 |
| 73 | 0.63 | — |
| 74 | 0.08 | — |
| 75 | 0.08 | 0.08 |
| 76 | 0.16 | — |
| 77 | 0.16 | — |
| 78 | 0.16 | — |
| 79 | 0.02 | 0.04 |
| 81 | 0.04 | 0.31 |
| 82 | 0.16 | — |
| 84 | 0.16 | 0.63 |
| 85 | 0.08 | 0.04 |
| 86 | 0.31 | 1.25 |
| 87 | 0.31 | 0.63 |
| 90 | 0.04 | 0.31 |
| 91 | 0.08 | — |
| 92 | 0.63 | — |
| 94 | 0.08 | 0.08 |
| 98 | 0.16 | 0.16 |
| 100 | 0.31 | 0.63 |
| 101 | 0.31 | — |
| 102 | 0.16 | 1.25 |
| 103 | 0.08 | 0.63 |
| 104 | 0.16 | — |
| 105 | 0.16 | — |
| 106 | 0.63 | — |

In view of their antihistaminic and serotonin-antagonistic properties, the compounds of formula (I) and their acid-addition salts are very useful in the treatment of allergic diseases such as, for example, allergic rhinitis, allergic conjunctivities, chronic urticaria, allergic astma and the like.

In view of the useful pharmacological properties the subject compounds may be formulated into various pharmaceutical forms for administration purposes. To prepare the pharmaceutical compositions of this invention, a pharmaceutically effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed.

For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution.

Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following formulations exemplify typical pharmaceutical compositions in dosage unit form suitable for systemic administration to animal and human subjects in accordance with the present invention. These examples are given to illustrate and not to limit the scope of the present invention.

"Active ingredient" (A.I.) as used throughout these examples relates to a compound of formula (I), a possible stereochemically isomeric form or pharmaceutically acceptable acid addition salt thereof.

EXAMPLE 62: ORAL DROPS

500 Grams of the A.I. was dissolved in 0.5 liters of 2-hydroxypropanoic acid and 1.5 liters of the polyethylene glycol at 60°–80° C. After cooling to 30°–40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

EXAMPLE 63: ORAL SOLUTION

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

EXAMPLE 64: CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

EXAMPLE 65: FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 milliliters of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 milligrams of the active ingredient.

Coating

To a solution of 10 grams methyl cellulose in 75 milliliters of denaturated ethanol there was added a solution of 5 grams of ethyl cellulose in 150 milliliters of dichloromethane. There there were added 75 millileters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109) and the whole was homogenated.

The tablet cores were coated with the thus obtained mixture in a coating apparatus.

EXAMPLE 66: INJECTABLE SOLUTION 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 propylene glycol and 4 grams of the A.I.. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

EXAMPLE 67: SUPPOSITORIES

3 Grams A.I. was dissolved in a solution of 3 grams 2,3-dihydroxybutanedioic acid in 25 milliliters polyethylene glycol 400. 12 Grams surfactant and triglycerides q.s. ad 300 grams were molten together. The latter mixture was mixed well with the former solution. The thus obtained mixture was poured onto moulds at a temperature of 37°–38° C. to form 100 suppositories each containing 30 milligrams of the active ingredient.

The present invention is also related with a method of treating allergic diseases in warm-blooded animals suffering from said allergic diseases by administering an effective anti-allergic amount of a compound of formula (I) or a pharmaceutically acceptable acid addition salt thereof.

Suitable doses administered daily to subjects are varying from 0.1 to 100 mg, more preferably from 1 to 50 mg.

What we claim is:

1. A chemical compound having the formula

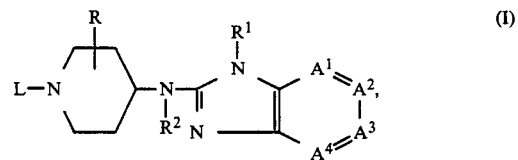

a pharmaceutically acceptable acid addition salt or a possible stereochemically isomeric form thereof, wherein:

$A^1=A^2-A^3=A^4$ is a bivalent radical having the formula

| | |
|---|---|
| —CH=CH—CH=CH—, | (a) |
| —N=CH—CH=CH—, | (b) |
| —CH=N—CH=CH—, | (c) |
| —CH=CH—N=CH—, | (d) |
| or | |
| —CH=CH—CH=N—, | (e) | wherein one or two hydrogen atoms in said radicals (a)-(e) may, each independently from each other, be replaced by halo, lower alkyl, lower alkyloxy, trifluoromethyl or hydroxy;

R is a member selected from the group consisting of hydrogen and lower alkyl;

$R^1$ is a member selected from the group consisting of hydrogen, alkyl, cycloalkyl, $Ar^1$ and lower alkyl substituted with one or two $Ar^1$ radicals;

$R^2$ is a member selected from the group consisting of hydrogen, lower alkyl, cycloalkyl, (lower alkyl)—CO—, (lower alkyl—O)—CO and $Ar^2$—lower alkyl;

L is a member selected from the group consisting of a radical of formula

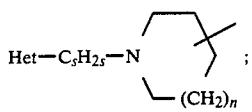

a radical of formula

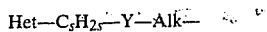

and a radical of formula

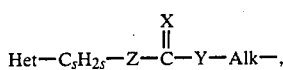

wherein n is 0 or the integer 1 or 2;
s is 0 or an integer of from 1 to 6 inclusive;
Alk is lower alkanediyl;
Y is O, S, $NR^3$ or a direct bond;
X is O, S, CH—$NO_2$ or $NR^4$;
Z is O, S, $NR^5$ or a direct bond; and
Het is a member selected from the group consisting of thiazolyl, 4,5-dihydrothiazolyl, oxazolyl, imidazolyl, tetrazolyl, 1,3,4-thiadiazolyl, benzimidazolyl, benzothiazolyl, benzoxazolyl, and indolyl whereby each of the said Het-radicals may optionally be substituted with up to two substituents selected from the group consisting of lower alkyl, $Ar^1$, $Ar^1$—lower alkyl, amino, (aminoiminomethyl)amino, mono- and di(lower alkyl)amino, $Ar^1$—amino, nitro and pyrimidinyl, said Het being connected to $C_sH_{2s}$ on a carbon atom;
said $R^3$ being hydrogen, lower alkyl, ($Ar^2$)lower alkyl, 2-lower alkyloxy-1,2-dioxoethyl or a radical of formula —C(=X)—$R^6$, $R^6$ being hydrogen, lower alkyl, $Ar^2$, $Ar^2$—lower alkyl, lower alkyloxy, $Ar^2$—lower alkyloxy, mono- or di(lower alkyl)amino, $Ar^2$—amino, $Ar^2$—lower alkylamino or $Ar^2$—lower alkyl(lower alkyl)amino;
said $R^4$ being hydrogen, lower alkyl, cyano, nitro, $Ar^2$—sulfonyl, lower alkylsulfonyl, lower alkylcarbonyl or $Ar^2$—carbonyl; and
said $R^5$ being hydrogen or lower alkyl; provided that:
(i) when $A^1$=$A^2$—$A^3$=$A^4$ is a bivalent radical of formula (a) or (b), then Het is other than 1-(lower alkyl)pyrrolyl;
(ii) when $A^1$=$A^2$—$A^3$=$A^4$ is a bivalent radical of formula (a) or (b) and L is a radical of formula (g) wherein s is 0 and Y is $NR^3$, then Het is other than 1H-benzimidazol-2-yl or $Ar^1$—Loweralkyl-1H-benzimidazol-2-yl;
wherein $Ar^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and lower alkyl—CO—; thienyl; halothienyl; furanyl; lower alkyl substituted furanyl; pyridinyl; pyrazinyl; thiazolyl and imidazolyl optionally substituted by lower alkyl; and wherein $Ar^2$ is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)CO.

2. A chemical compound according to claim 1 wherein L is a radical of formula (g) or (h).

3. An anti-allergic composition comprising suitable pharmaceutical carriers and as active ingredient an anti-allergic effective amount of a compound having the formula

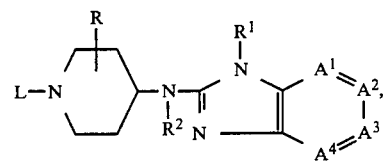

a pharmaceutically acceptable acid addition salt or a possible stereochemically isomeric form thereof, wherein:

$A^1$=$A^2$—$A^3$=$A^4$ is a bivalent radical having the formula

| | |
|---|---|
| —CH=CH—CH=CH—, | (a) |
| —N=CH—CH=CH—, | (b) |
| —CH=N—CH=CH—, | (c) |
| —CH=CH—N=CH—, | (d) | or

| | |
|---|---|
| —CH=CH—CH=N—, | (e) | wherein one or two hydrogen atoms in said radicals (a)-(e) may, each independently from each other, be replaced by halo, lower alkyl, lower alkyloxy, trifluoromethyl or hydroxy;
R is a member selected from the group consisting of hydrogen and lower alkyl;
$R^1$ is a member selected from the group consisting of hydrogen, alkyl, cycloalkyl, $Ar^1$ and lower alkyl substituted with one or two $Ar^1$ radicals;
$R^2$ is a member selected from the group consisting of hydrogen, lower alkyl, cycloalkyl, (lower alkyl)—CO—, (lower alkyl—O)—CO and $Ar^2$—lower alkyl;
L is a member selected from the group consisting of a radical of formula

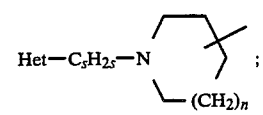

a radical of formula

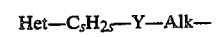

and a radical of formula

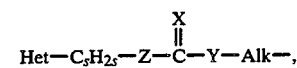

wherein n is 0 or the integer 1 or 2;
s is 0 or an integer of from 1 to 6 inclusive;

Alk is lower alkanediyl;
Y is O, S, NR$^3$ or a direct bond;
X is O, S, CH—NO$_2$ or NR$^4$;
Z is O, S, NR$^5$ or a direct bond; and
Het is a member selected from the group consisting of thiazolyl, 4,5-dihydrothiazolyl, oxazolyl, imidazolyl, tetrazolyl, 1,3,4-thiadiazolyl, benzimidazolyl, benzothiazolyl, benzoxazolyl, and indolyl whereby each of the said Het-radicals may optionally be substituted with up to two substituents selected from the group consisting of lower alkyl, Ar$^1$, Ar$^1$—lower alkyl, amino, (aminoiminomethyl)amino, mono- and di(lower alkyl)amino, Ar$^1$—amino, nitro and pyrimidinyl, said Het being connected to C$_s$H$_{2s}$ on a carbon atom;
said R$^3$ being hydrogen, lower alkyl, (Ar$^2$)lower alkyl, 2-lower alkyloxy-1,2-dioxoethyl or a radical of formula —C(=X)—R$^6$, R$^6$ being hydrogen, lower alkyl, Ar$^2$, Ar$^2$—lower alkyl, lower alkyloxy, Ar$^2$—lower alkyloxy, mono- or di(lower alkyl)amino, Ar$^2$—amino, Ar$^2$—lower alkylamino or Ar$^2$—lower alkyl(lower alkyl)amino;
said R$^4$ being hydrogen, lower alkyl, cyano, nitro, Ar$^2$—sulfonyl, lower alkylsulfonyl, lower alkylcarbonyl or Ar$^2$—carbonyl; and
said R$^5$ being hydrogen or lower alkyl; provided that:
(i) when A$^1$=A$^2$—A$^3$=A$^4$ is a bivalent radical of formula (a) or (b), then Het is other than 1-(lower alkyl)pyrrolyl;
(ii) when A$^1$=A$^2$—A$^3$=A$^4$ is a bivalent radical of formula (a) or (b) and L is a radical of formula (g) wherein s is 0 and Y is NR$^3$, then Het is other than 1H-benzimidazol-2-yl or Ar$^1$-loweralkyl-1H-benzimidazol-2yl;
wherein Ar$^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and lower alkyl—CO—; thienyl; halothienyl; furanyl; lower alkyl substituted furanyl; pyridinyl; pyrazinyl; thiazolyl and imidazolyl optionally substituted by lower alkyl; and wherein Ar$^2$ is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)CO.

4. An anti-allergic composition according to claim 3 wherein L is a radical of Formula (g) or (h).

5. A method of treating allergic diseases in warm-blooded animals suffering from same which method comprises the systemic administration to warm-blooded animals of an effective anti-allergic amount of a compound having the formula

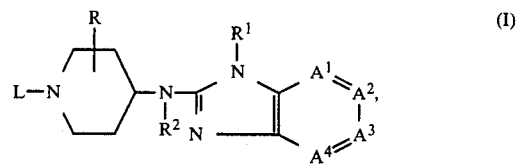

a pharmaceutically acceptable acid addition salt or a possible stereochemically isomeric form thereof, wherein:

A$^1$=A$^2$—A$^3$=A$^4$ is a bivalent radical having the formula

—CH=CH—CH=CH—,                (a)

—N=CH—CH=CH—,                 (b)

—CH=N—CH=CH—,                 (c)

—CH=CH—N=CH—,                 (d)

or

—CH=CH—CH=N—,                 (e)

wherein one or two hydrogen atoms in said radicals (a)-(e) may, each independently from each other, be replaced by halo, lower alkyl, lower alkyloxy, trifluoromethyl or hydroxy;
R is a member selected from the group consisting of hydrogen and lower alkyl;
R$^1$ is a member selected from the group consisting of hydrogen, alkyl, cycloalkyl, Ar$^1$ and lower alkyl substituted with one or two Ar$^1$ radicals;
R$^2$ is a member selected from the group consisting of hydrogen, lower alkyl, cycloalkyl, (lower alkyl)—CO—, (lower alkyl—O)—CO and Ar$^2$—lower alkyl;
L is a member selected from the group consisting of a radical of formula

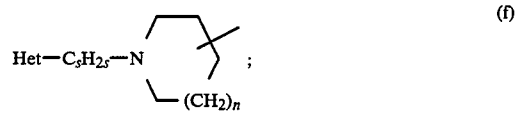

a radical of formula

Het—C$_s$H$_{2s}$—Y—Alk—          (g);

and a radical of formula

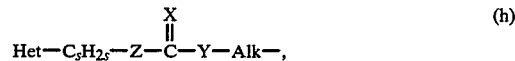

wherein n is 0 or the integer 1 or 2;
s is 0 or an integer of from 1 to 6 inclusive;
Alk is lower alkanediyl;
Y is O, S, NR$^3$ or a direct bond;
X is O, S, CH—NO$_2$ or NR$^4$;
Z is O, S, NR$^5$ or a direct bond; and
Het is a member selected from the group consisting of thiazolyl, 4,5-dihydrothiazolyl, oxazolyl, imidazolyl, tetrazolyl, 1,3,4-thiadiazolyl, benzimidazolyl, benzothiazolyl, benzoxazolyl, and indolyl whereby each of the said Het-radicals may optionally be substituted with up to two substituents selected from the group consisting of lower alkyl, $Ar^1$, $Ar^1$, $Ar^1$—lower alkyl, amino, (aminoiminomethyl)amino, mono- and di(lower alkyl)amino, $Ar^1$—amino, nitro and pyrimidinyl, said Het being connected to $C_sH_{2s}$ on a carbon atom;

said $R^3$ being hydrogen, lower alkyl, ($Ar^2$)lower alkyl, 2-lower alkyloxy-1,2-dioxoethyl or a radical of formula $-C(=X)-R^6$, $R^6$ being hydrogen, lower alkyl, $Ar^2$, $Ar^2$—lower alkyl, lower alkyloxy, $Ar^2$—lower alkyloxy, mono- or di(lower alkyl)amino, $Ar^2$—amino, $Ar^2$—lower alkylamino or $Ar^2$—lower alkyl(lower alkyl)amino;

said $R^4$ being hydrogen, lower alkyl, cyano, nitro, $Ar^2$—sulfonyl, lower alkylsulfonyl, lower alkylcarbonyl or $Ar^2$—carbonyl; and said $R^5$ being hydrogen or lower alkyl; provided that:
(i) when $A^1=A^2-A^3=A^4$ is a bivalent radical of formula (a) or (b), then Het is other than 1-(lower alkyl)pyrrolyl;
(ii) when $A^1=A^2-A^3=A^4$ is a bivalent radical of formula (a) or (b) and L is a radical of formula (g) wherein S is 0 and Y is $NR^3$, then Het is other than 1H-benzimidazol-2-yl or $Ar^1$-loweralkyl-1H-benzimidazol-2-yl;

wherein $Ar^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and lower alkyl—CO—; thienyl; halothienyl; furanyl; lower alkyl substituted furanyl; pyridinyl; pyrazinyl; thiazolyl and imidazolyl optionally substituted by lower alkyl; and wherein $Ar^2$ is a member selected from the group consisting of phenyl being optionally substituted with up to three substituents each independently selected from the group consisting of halo, hydroxy, nitro, cyano, trifluoromethyl, lower alkyl lower alkyloxy, lower alkylthio, mercapto, amino, mono- and di(lower alkyl)amino, carboxyl, lower alkyloxycarbonyl and (lower alkyl)CO.

6. A method according to claim 5 wherein L is a radical of formula (g) or (h).

* * * * *